(12) United States Patent
Ceglinski et al.

(10) Patent No.: US 11,579,077 B2
(45) Date of Patent: Feb. 14, 2023

(54) DEVICE AND METHOD FOR MEASURING MOISTURE IN CORN ON EAR

(71) Applicant: Monsanto Technology LLC, St. Louis, MO (US)

(72) Inventors: Jarrett R. Ceglinski, St. Louis, MO (US); Amanuel G. Ghebretinsae, Chesterfield, MO (US); Jiha Kim, Seoul (KR); Richard M. Leimgruber, Chesterfield, MO (US); Tracy L. Whitehead, Pacific, MO (US)

(73) Assignee: Monsanto Technology LLC, St. Louis, MO (US)

( * ) Notice: Subject to any disclaimer, the term of this patent is extended or adjusted under 35 U.S.C. 154(b) by 538 days.

(21) Appl. No.: 16/625,582

(22) PCT Filed: Jun. 19, 2018

(86) PCT No.: PCT/US2018/038168
§ 371 (c)(1),
(2) Date: Dec. 20, 2019

(87) PCT Pub. No.: WO2018/236787
PCT Pub. Date: Dec. 27, 2018

(65) Prior Publication Data
US 2022/0034799 A1    Feb. 3, 2022

Related U.S. Application Data

(60) Provisional application No. 62/522,485, filed on Jun. 20, 2017.

(51) Int. Cl.
*G01J 3/02*    (2006.01)
*G01N 21/3554*    (2014.01)
(Continued)

(52) U.S. Cl.
CPC ........ *G01N 21/3554* (2013.01); *G01J 3/0272* (2013.01); *G01N 21/359* (2013.01);
(Continued)

(58) Field of Classification Search
CPC ........ G01J 3/28; G01J 3/14; G01J 3/18; G01J 3/02; G01J 3/0272; G01N 21/3554;
(Continued)

(56) References Cited

U.S. PATENT DOCUMENTS 4,954,783 A    9/1990    Spry
7,660,698 B1 *    2/2010    Seelig ............... G01B 7/10
                                                              702/170

(Continued)

FOREIGN PATENT DOCUMENTS

CN    1982871    6/2006
CN    102033043    4/2011
(Continued)

OTHER PUBLICATIONS

Agricultrual Instruments—Chlorophyll Meter Manufacturer from Coimbatore, Portable Plant Nutrition Analyzer, Aug. 10, 2018, 2 pages, http://www.instrumentsmart.com/agricultural-instruments.html.

(Continued)

*Primary Examiner* — Abdullahi Nur
(74) *Attorney, Agent, or Firm* — Harness, Dickey & Pierce, P.L.C.

(57)    ABSTRACT

In a method of measuring moisture in corn, an ear of corn is operatively coupled to a moisture meter and an amount of moisture is determined while the ear of corn is being grown on a corn plant. The moisture meter can use a spectrometry to determine the amount of moisture in the corn. A moisture meter includes a corn interface configured to conformingly engage the ear of corn when pressed against the ear of corn (Continued)

to form an optical seal about an opening through which the spectrometer determines the amount of moisture in the corn to inhibit ambient light from passing between the corn interface and the ear of corn into the at least one opening.

18 Claims, 17 Drawing Sheets

(51) Int. Cl.
    *G01N 21/359*     (2014.01)
    *G01N 21/84*     (2006.01)
    *G01N 33/02*     (2006.01)

(52) U.S. Cl.
    CPC .......... *G01N 21/84* (2013.01); *G01N 33/025* (2013.01); *G01N 2021/8466* (2013.01); *G01N 2201/0221* (2013.01); *G01N 2201/0646* (2013.01)

(58) Field of Classification Search
    CPC .... G01N 21/359; G01N 21/84; G01N 33/025; G01N 2021/8466; G01N 2201/0221; G01N 2201/0646
    See application file for complete search history.

(56) References Cited

U.S. PATENT DOCUMENTS

| | | | |
|---|---|---|---|
| 2012/0061586 A1* | 3/2012 | Yao | G01N 21/6486 250/461.1 |
| 2012/0260618 A1 | 10/2012 | Alley et al. | |
| 2016/0300363 A1 | 10/2016 | Darrell et al. | |
| 2018/0218215 A1* | 8/2018 | Quenard | H04N 5/2354 |

FOREIGN PATENT DOCUMENTS

| | | |
|---|---|---|
| CN | 102331446 | 1/2012 |
| WO | 2017/021285 A1 | 2/2017 |

OTHER PUBLICATIONS

Extended European Search Report for European Application No. 18819772.7, 12 pages, dated Jan. 27, 2021, Munich, Germany.
Zhhao Pengfei et al., Rapid On-Line Non-Destructive Detection of the Moisture Content of Corn Ear by Bioelectrical Impedance Spectroscopy, http://www.ijabe.org, Int J Agrec & Biol Eng, Dec. 2015, vol. 8 No. 6, pp. 37-45, XP055766268.
CN2021121301881950: Office Action and Search Report dated Dec. 16, 2021 (17 pages). CN2021121301881950 is a National Phase of PCT Patent Application PCT/US2018/038168, which has the same priority claim as the instant application.
Feng, J. et al., Assessment of Yellow-Fleshed Kiwifruit (*Actinidia chinensis* 'Hort16A') Quality in Pre- and Post-harvest Conditions Using a Portable Near-infrared Spectrometer, Postharvest Biology and Technology, HORTSCIENCE vol. 46 No. 1 pp. 57-63, Jan. 2011, abstract, figure 1, pp. 57-58, The New Zealand Institute for Plant & Food Research Limited.
Instrumentsmart, Agricultrual Instruments, Mar. 2, 2017, Retrieved on Aug. 10, 2018 from the internet at https://web.archive.ort/web/20170302141349/http://www.instrumentsmart.com/agricultural-instruments.html; p. 1, paragraphs 2-3.
Lui, Y, Research progress of the portable and online NIR Detection for Internal Quality of Fruits, Dec. 4, 2019, retrieved on Aug. 10, 2018 from the internet at http://axis123.com/mall/m_filedown.php?fl_goid+4090&btn_type+catalogue, pp. 7-10, 12, 14.
International Search Report and Written Opinion for PCT Application No. PCT/US18/38168, dated Aug. 31, 2018, 11 pages, United States.
Charles R. Hurburgh, Jr., et al., Corn Moisture Measurement Accuracy, American Society of Agricultural Engineers, 1985, pp. 0634-640, Iowa State University, Agriculture and Biosystems Engineering.
Sunforest Co., Ltd, Sunforest H-100 Series, Portable Non-Destructive Fruit Quality Meter, as early as Aug. 1, 2016, 2 pages, Korea.

* cited by examiner

DEVICE AND METHOD FOR MEASURING MOISTURE IN CORN ON EAR

CROSS-REFERENCE TO RELATED APPLICATION

This application claims priority to U.S. Provisional Patent Application Ser. No. 62/522,485, filed Jun. 20, 2017 and entitled "DEVICE AND METHOD FOR MEASURING MOISTURE IN CORN ON EAR," which is hereby incorporated by reference in its entirety.

FIELD OF THE DISCLOSURE

The present disclosure relates to a device and method for measuring moisture in corn and, more specifically, to a device and method for measuring moisture in kernels on an ear of corn, such as an ear of corn growing on a corn plant.

BACKGROUND

The amount of moisture (e.g., water) in corn is a useful proxy for the corn's nutritional content. As the amount of moisture increases, nutritional content decreases. Accordingly, moisture content is often measured to determine the price of corn at sale. When the amount of moisture is higher than normal, the price of the corn is typically discounted. To maximize the price of corn at sale, users measure moisture before harvest and try to harvest the crop at an optimal moisture level. Conventional methods of measuring moisture involve sampling and shelling a few ears of corn in each field and measuring moisture content using a benchtop instrument remote from the field. Certain instruments measure moisture by drying the corn and measuring weight loss on drying. Other instruments directly measure the amount of water in the corn by chemical reaction (the Karl Fischer method). Still other instruments measure moisture by transmitting signals such as radio frequency signals through the harvested corn and analyzing the effect of the corn on the signals.

SUMMARY OF THE DISCLOSURE

In one aspect, a method of measuring moisture in corn comprises operatively coupling an ear of corn to a spectrometer while the ear of corn is being grown on a corn plant. An amount of moisture in the ear of corn is determined with the spectrometer while the ear of corn is being grown on the corn plant.

In another aspect, a corn interface for operatively coupling a spectrometer to an ear of corn for measuring an amount of moisture in the corn comprises a spectrometer interface configured to attach to the spectrometer. A gasket is supported on the spectrometer interface. The gasket has an exterior surface, an interior surface defining an interior space for receiving the ear of corn, and a thickness extending between the interior and exterior surfaces. The gasket defines an opening that extends through the thickness of the gasket from the exterior surface through the interior surface. The opening is shaped and arranged to be aligned with at least one of a radiation source and a radiation detector of the spectrometer when the spectrometer mount is attached to the spectrometer. The interior surface of the gasket is configured to conformingly engage the ear of corn when pressed against the ear of corn to form an optical seal about the opening between the ear of corn and said at least one of a radiation source and a radiation detector of the spectrometer.

In still another aspect, a moisture meter for measuring moisture in corn comprises a hand-held housing. A corn interface is mounted on the hand-held housing and has a thickness. The corn interface defines at least one opening extending through the thickness. The corn interface is configured to operatively couple to an ear of corn to form an optical seal around the at least one opening between the ear of corn and the corn interface to inhibit ambient light from passing between the corn interface and the ear of corn into the at least one opening. A radiation source is supported on the hand-held housing and configured to convey radiation through the at least one opening to the corn when the corn is operatively coupled to the moisture meter. A detector is mounted on the hand-held housing and configured to detect a radiation spectrum passing through the at least one opening and to generate a signal representative of the detected radiation spectrum. A measurement processor is configured to receive the signal from the detector and to determine an amount of moisture in the corn based on the signal.

Other features will be in part apparent and in part pointed out hereinafter.

BRIEF DESCRIPTION THE DRAWINGS

Corresponding reference characters indicate corresponding parts throughout the drawings.

DETAILED DESCRIPTION

Figure 1:
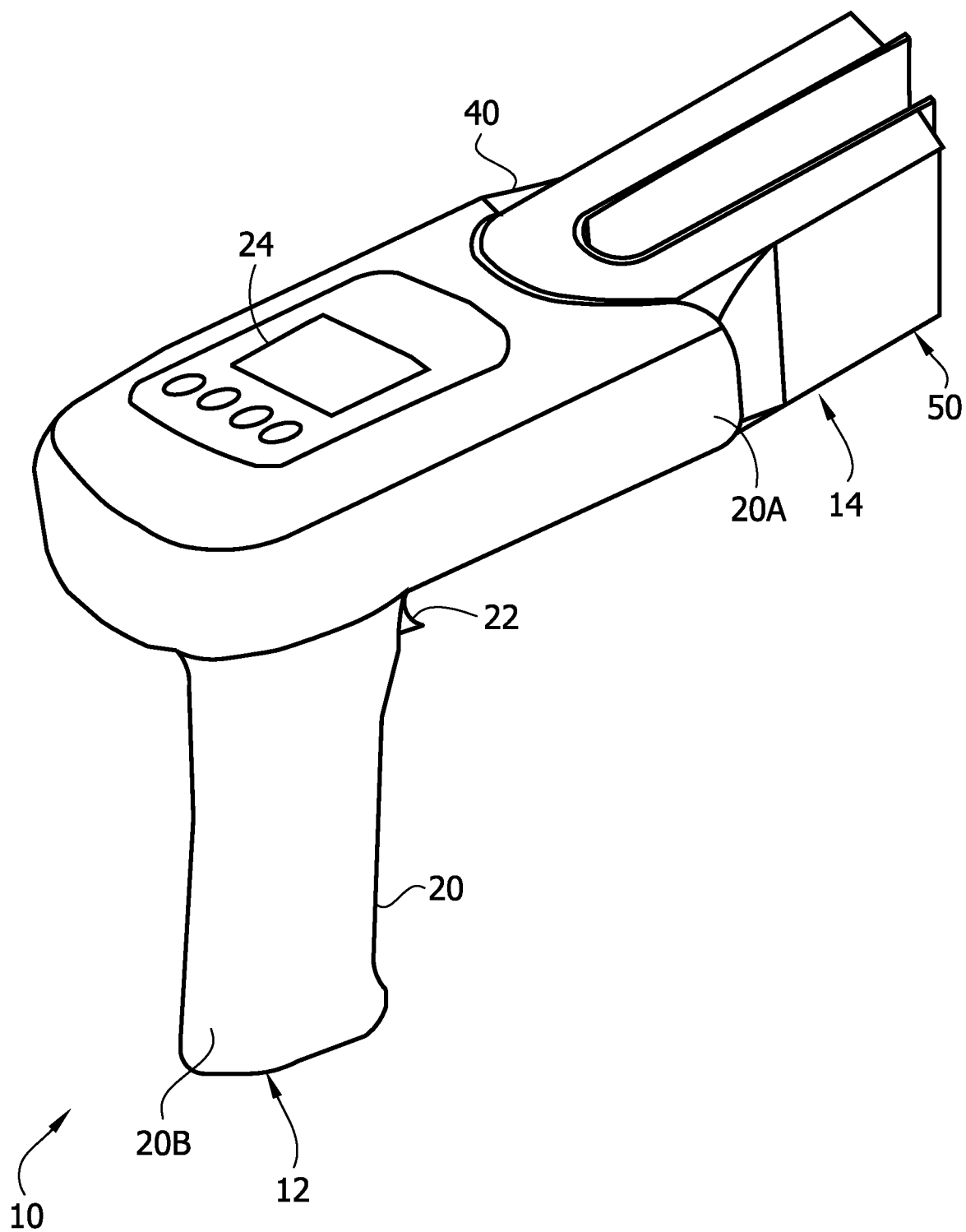
FIG. 1 is a perspective of one embodiment of a moisture meter for measuring moisture in corn.
Figure 2:
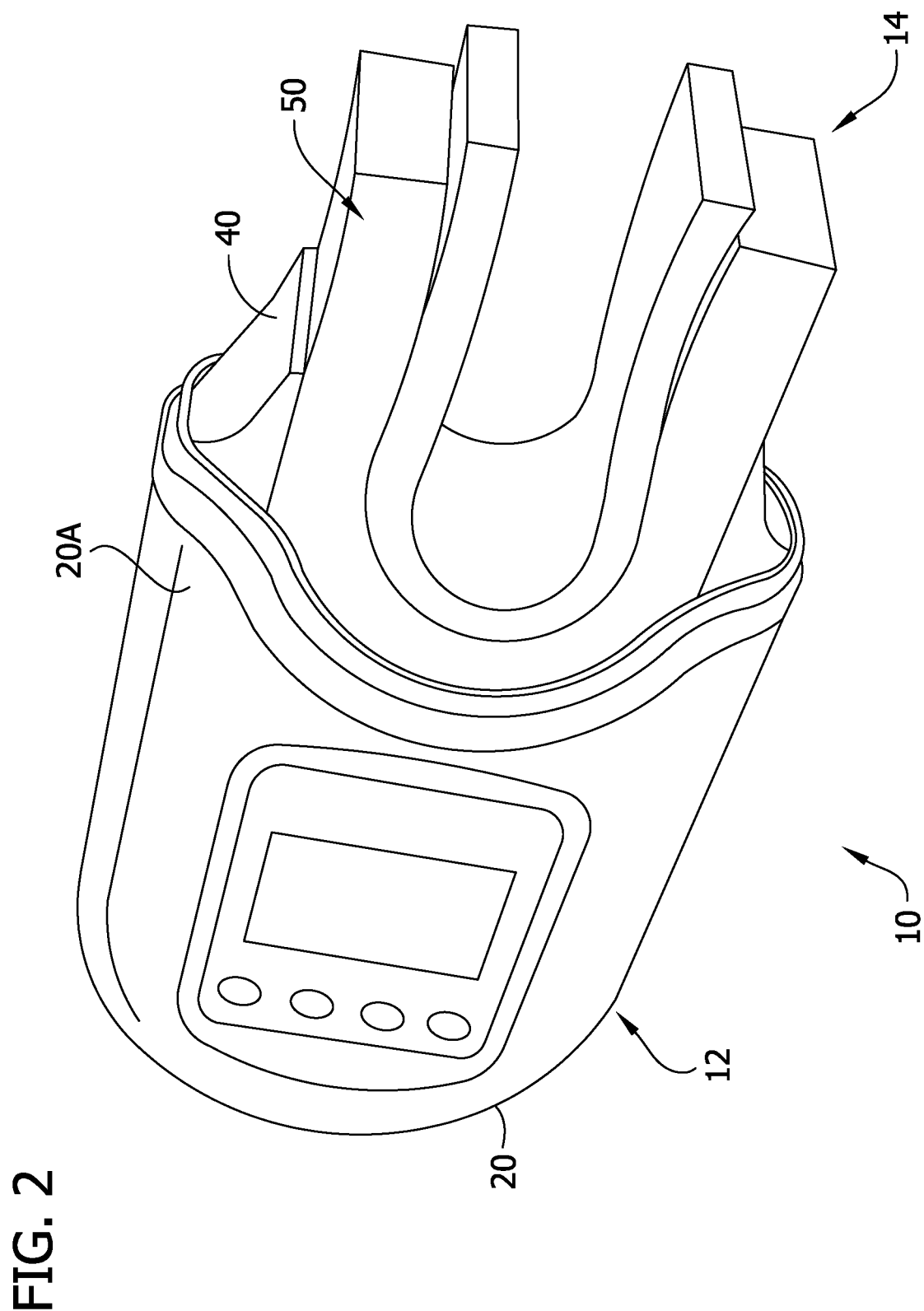
FIG. 2 is a top view of the moisture meter.
Figure 3:
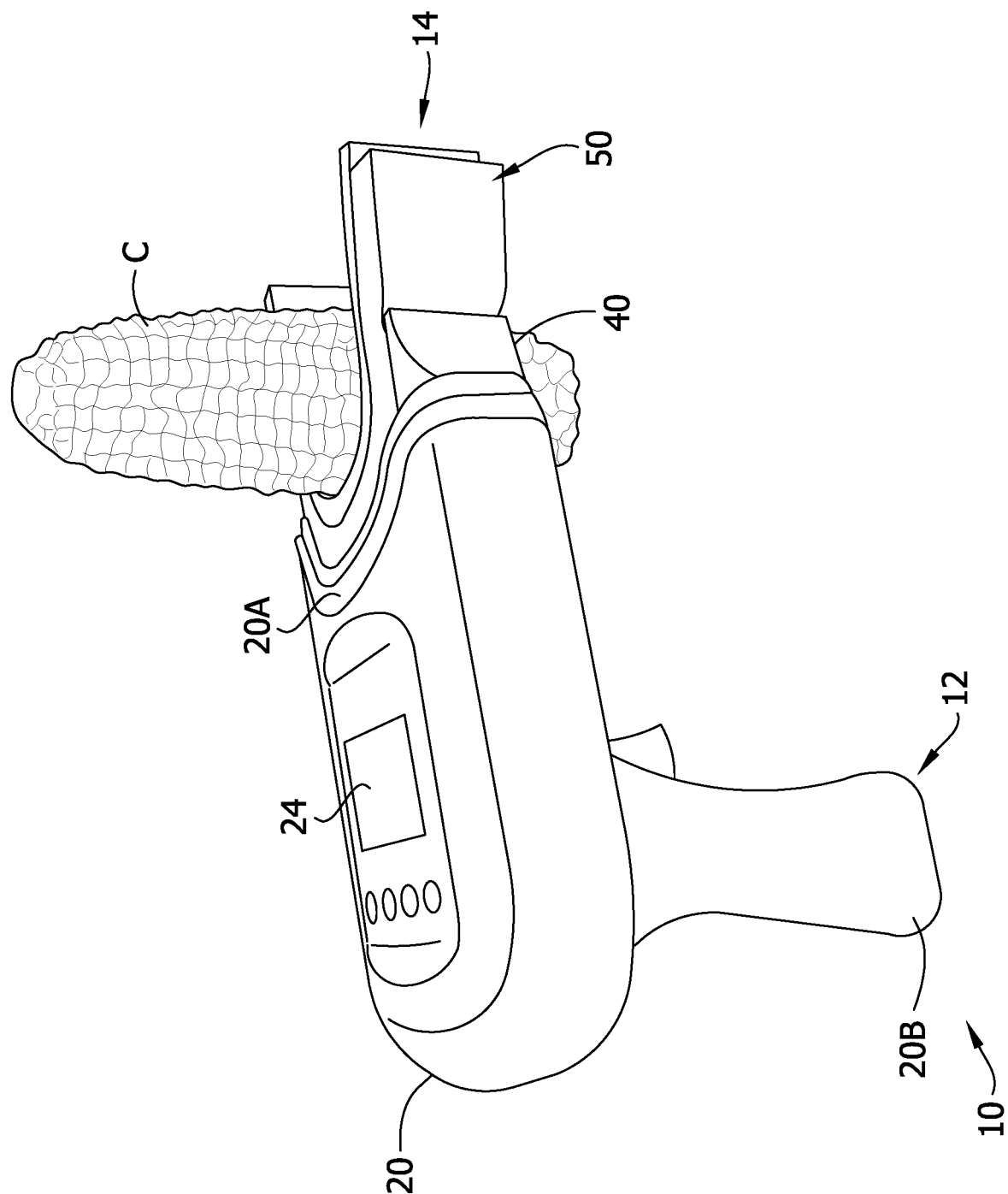
FIG. 3 is a perspective of the moisture meter in use measuring moisture in an ear of corn.

Referring to FIGS. 1-3, a moisture meter for measuring an amount of moisture in kernels of an ear of corn C (e.g., field corn or sweet corn; broadly, a crop) is generally indicated at reference number 10. It will be understood that the teachings of the illustrated moisture meter 10 set forth herein, while specially configured for measuring an amount of moisture in corn C in the illustrated embodiment, could be adapted for use in measuring other properties and/or other crops growing in a field in other embodiments. The moisture meter 10 comprises a handheld spectrometer (broadly, a portable composition measurement instrument), generally indicated at 12; and a corn interface, generally indicated at 14, for operatively coupling the ear of corn C to the spectrometer to enable the spectrometer to measure the amount of moisture in the corn. In the illustrated embodiment, the spectrometer 12 comprises a near infrared (NIR) spectrometer configured to measure the amount of moisture in the corn C using NIR spectroscopy. As an example, suitable spectrometer hardware is an NIR moisture gun sold by Sunforest of Incheon, South Korea, under the name H-100C. However, it will be understood that other portable composition measurement instruments, such as other NIR spectrometers or other types of measurement instruments can be used in other embodiments. As will be explained in further detail below, the corn interface 14 is configured to couple to the corn C to form an optical seal between the ear of corn C and the spectrometer 12 to limit the effect of ambient light on the moisture measurement. As further explained below, the illustrated moisture meter 10 is configured to non-destructively measure the moisture content of corn C growing on ears in the field, without removing the corn and thus sacrificing the corn from the later harvest, in order to obtain a sample measurement.

Figure 4:
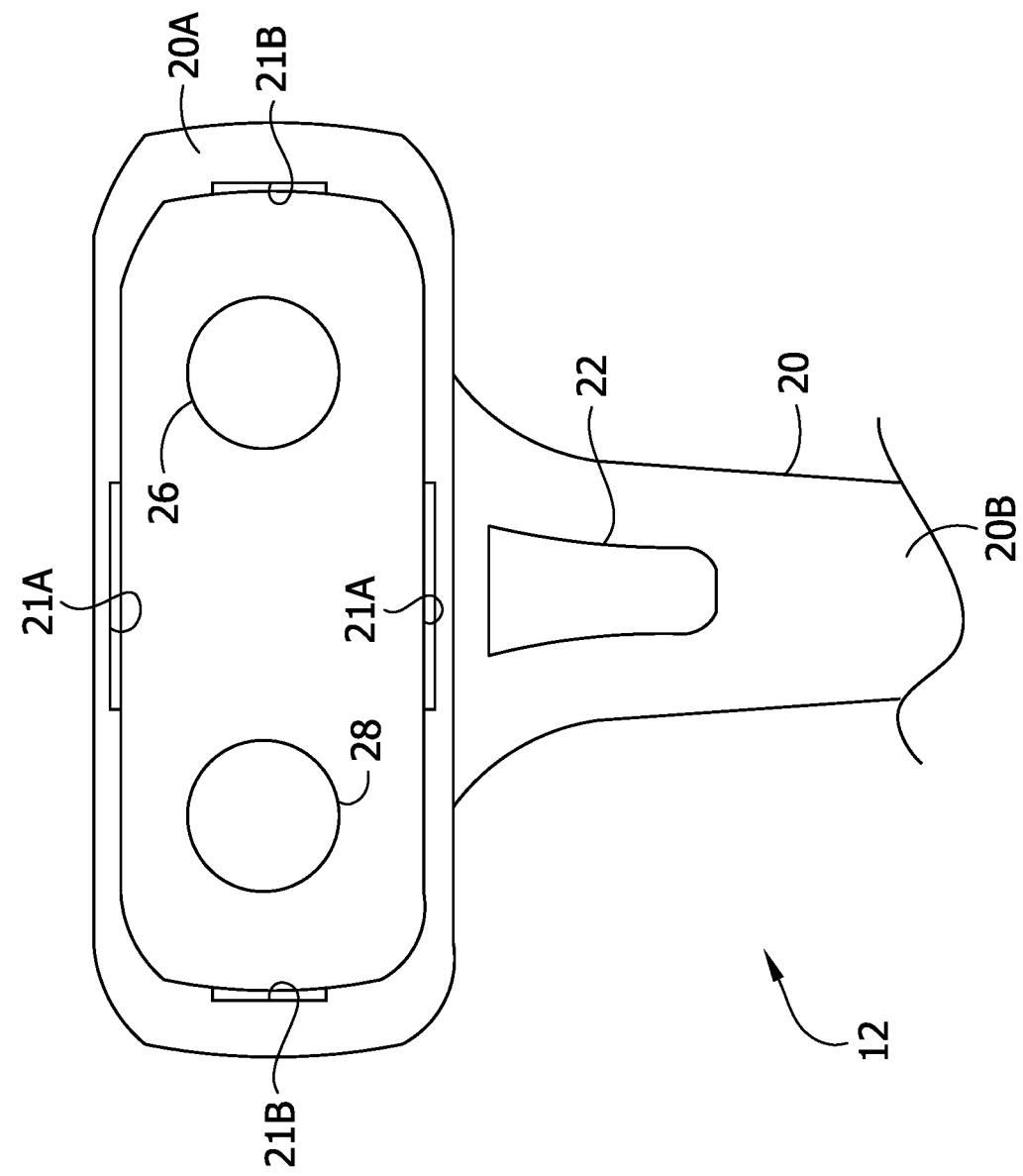
FIG. 4 is a front elevational view of a spectrometer of the moisture meter with a corn interface of the moisture meter removed.

Referring to FIGS. 1-4, the spectrometer 12 comprises a hand-held housing 20 (broadly, a support). The housing 20 has a distal (front) end portion 20A that faces the corn C in use. The distal end portion 20A defines at least one mount configured to mount the corn interface 14 at an operative position with respect to the spectrometer 12 to enable the spectrometer to measure the corn C when the corn is coupled to the corn interface. As shown in FIG. 4, the illustrated mount includes top and bottom mounting recesses 21A, and first and second side mounting recesses 21B. As explained below, the mounting recesses 21A, 21B receive corresponding tabs 41A, 41B of the corn interface 14 for use in mounting the corn interface 14 to the mount. Other ways of mounting or securing the corn interface 14 to the spectrometer 12 can be used in other embodiments.

In the illustrated embodiment, the housing 20 defines a pistol grip 20B, which forms a proximal (rear) end portion of the housing and is configured to be grasped by a hand of a user for holding the moisture meter 10. Thus, the spectrometer 10 is a handheld and portable device. As shown in FIG. 1, a trigger 22 (broadly, an actuator) is supported on the pistol grip 20B for being selectively depressed to actuate the spectrometer 12. As explained below, when the trigger 22 is depressed, the spectrometer 12 transmits radiation toward a target (e.g., the corn C), detects a radiation spectrum of the target (e.g., a radiation spectrum such as an NIR spectrum affected by the target absorbing, reflecting, and/or transmitting portions of the transmitted radiation), analyzes data representative of the detected radiation spectrum to determine an amount of water in the target, and displays an indication of the determined amount of water on a local display 24 mounted on the housing 20. The moisture value is also stored in the NIR device (memory 32) and can be retrieved, using a USB cable connecting the NIR device to a laptop or PC, in a csv format file.

Figure 5:
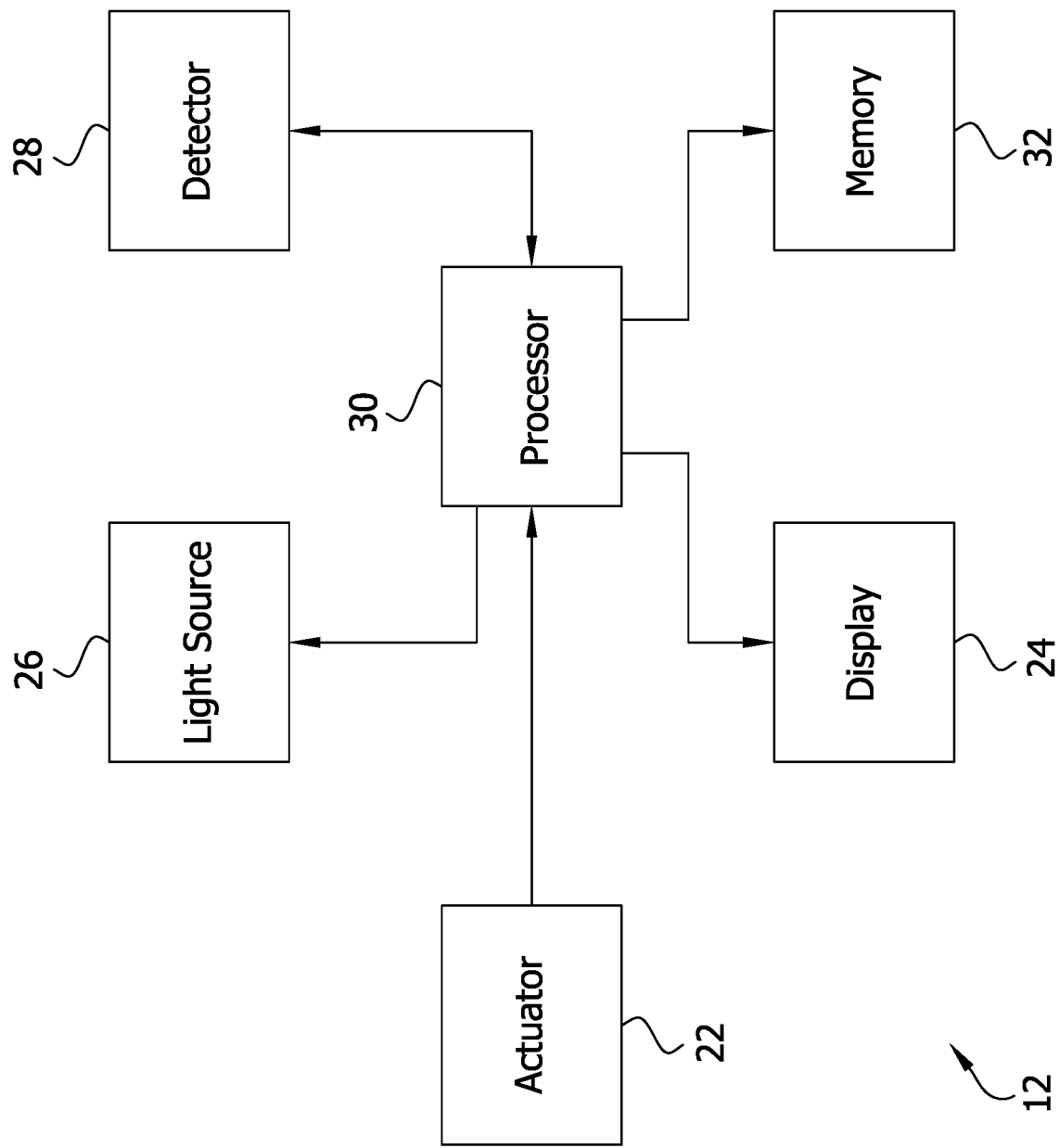
FIG. 5 is a schematic block diagram of components of the spectrometer.

Referring to FIGS. 4-5, the spectrometer 12 includes a radiation source 26 (e.g., a source of electromagnetic radiation) and a radiation detector 28 mounted on the distal end portion 20A of the housing 20. The radiation source 26 of the present embodiment is configured to convey, as an example, near-infrared radiation (NIR) toward a target. As explained below, the corn interface 14 is configured to couple the ear of corn C to the spectrometer 12 such that the radiation source 26 conveys radiation toward the ear of corn. In one or more embodiment, any suitable radiation source can be used (e.g., a light emitting diode, a halogen bulb, an incandescent bulb, a laser, a light pipe, etc.) to emit radiation. Certain radiation sources are configured to convey broad and bright collimated beams of radiation toward the corn C so that at least some of the radiation is conveyed through the interstices between the kernels to the sides of the kernels.

The radiation detector 28 is configured to detect a radiation spectrum. In particular, the illustrated radiation detector 28 is configured to detect radiation reflected from the ear of corn that originated from incident radiation from the radiation source 26. For example, in one embodiment, the radiation detector 28 may comprise a CMOS APS sensor configured for sensing an electromagnetic spectrum. The radiation detector 28 is mounted on the housing 20 to detect a radiation spectrum from the location to which the radiation source 26 is configured to generate radiation (e.g., the target corn C). In the illustrated embodiment, the radiation detector 28 is configured to detect radiation in the NIR spectrum, for example, electromagnetic radiation having a wavelength of from about 650 nm to about 950 nm. The radiation detector 28 is generates a signal representative of the detected radiation spectrum. As explained below, a measurement processor 30 (FIG. 5) coupled to suitable memory 32 is operatively connected to the radiation detector 30 to receive the signal and analyze the signal to determine an amount of moisture in the corn C. In the illustrated embodiment, the measurement processor 30 is enclosed inside the housing 20 of the spectrometer 12. In other embodiments, the spectrometer can be configured for connection to a remote processor for performing one or more measurement processing steps. The local measurement processor 30 (or other processor) is operatively connected to the trigger 22 and is configured as a controller to activate the radiation source 26 and the detector 28 when the trigger is depressed. A power supply (e.g., a battery; not shown) is also supported in the housing 20 and connected to the processor 30, the radiation source 26, and the detector 28 to power the spectrometer 12.

In general, the measurement processor 30 is configured for processing the signal from the radiation detector 28 to determine material properties of the target. As is known in the art, different compositions interact with radiation in different ways. For example, water absorbs radiation at certain wavelengths, including radiation at a wavelength of about 698 nm. In the illustrated embodiment, the measurement processor 30 is configured to analyze the signal from the radiation detector 28 to determine an amount of water in the corn C. For example, the measurement processor 30 may effectively determine an amount of radiation from the radiation source 26 at wavelengths in the NIR region from about 650 to about 950 nm that is absorbed by the corn C using the signal from the radiation detector 28, which is indicative of the amount of reflected radiation, and determine the amount of moisture in the corn C based on the determined amount of absorbed radiation. It is understood that the measurement processor 30 may only use the amount of reflected radiation to determine the amount of moisture in the corn C since the amount of absorbed radiation may be based on the amount of reflected radiation. In other embodiments, the measurement processor 30 can be programmed to determine other characteristics of the corn C or other crop using another parameter of the detected radiation. In yet other embodiments, different wavelengths within the entire NIR spectral range of about 780 nm to about 2800 nm may be utilized to determine other characteristics.

The measurement processor 30 is operatively connected to the display 24 to display the determined amount of moisture. In one embodiment, the measurement processor 30 is configured to determine and indicate the amount of moisture as a moisture percentage by weight of the corn C. In other embodiments, the measurement processor 30 can be configured to determine the amount of moisture in the corn C in other units of measure. The measurement processor 30 is further connected to a local memory 32. The measurement processor 30 is configured to store the signals from the detector 28 and/or the determined amount of moisture in the corn on the local memory 32 in the illustrated embodiment. Suitably, the spectrometer 12 can include an interface (e.g., a cable connector, a wireless transmitter, etc.) for connecting the memory 32 to a remote device (e.g., a computer, a mobile device, etc.) for conveying the data from the memory to the remote device.

Figure 6:
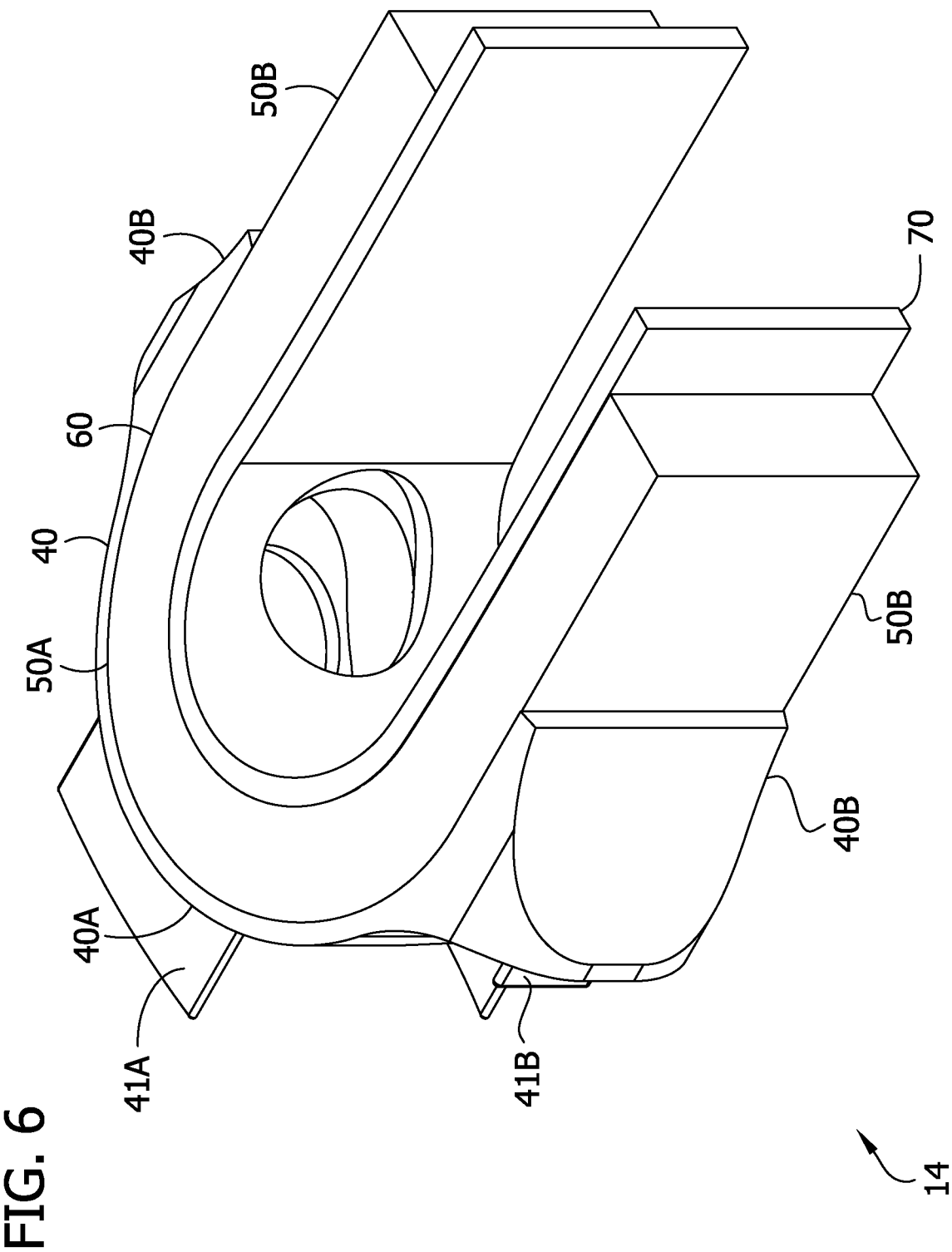
FIG. 6 is a perspective of the corn interface of the moisture meter.
Figure 7:
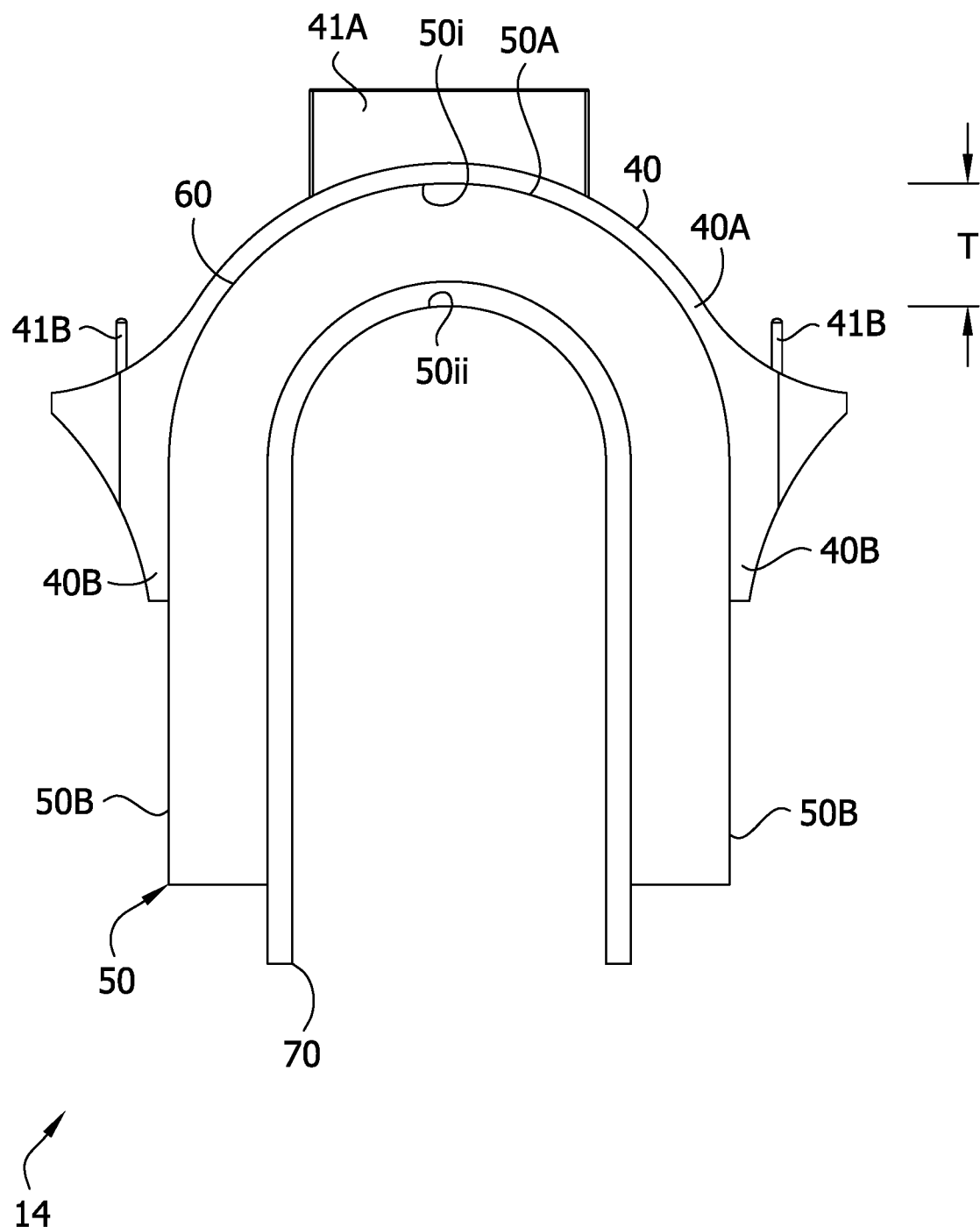
FIG. 7 is a top plan view of the corn interface.

Referring to FIGS. 6-7, the illustrated corn interface 14 comprises a mount interface 40 (broadly, a spectrometer interface) for mounting the corn interface on the mount of the spectrometer housing 20 in operative alignment with the radiation source 26 and the detector 28 of the spectrometer 12. The illustrated mount interface 40 comprises a U-shaped body having a generally arcuate proximal base portion 40A and first and second arm portions 40B extending from the base portion. In the illustrated embodiment, the mount interface 40 comprises a one-piece body of plastic or metal construction formed by 3-D printing, molding, additive manufacturing, machining, or any other suitable process. In other embodiments, the mount interface 40 may be constructed of more than one piece and/or using other manufacturing processes.

The mount interface 40 includes top and bottom mounting tabs 41A extending proximally from the base portion 40A, and first and second side mounting tabs 41B extending proximally from the arm portions 40B. The top and bottom mounting tabs 41A are configured to be inserted in the top and bottom mounting recesses 21A, and the side mounting tabs 41B are configured to be inserted in the side mounting recesses 21B of the housing 20. In one or more embodiments, the mounting tabs 41A, 41B are configured to attach the interface 14 to the spectrometer 12 when received in the recesses 21A, 21B. For example, the mounting tabs 41A, 41B can be configured for interlocking engagement, an interference fit, and/or a friction fit with the recesses 21A, 21B in certain embodiments. The tabs 41A, 41B may be suitably removable from the recesses 21A, 21B to permit a plurality of corn interfaces 14 of different sizes and/or designs to be interchangeably installed on the spectrometer 12. For example, referring to FIGS. 7 and 14, in one embodiment the measurement device 10 includes a plurality of interchangeable corn interfaces 14, 14' of different sizes, each having a mount interface 40 comprising a substantially identical mounting construction (e.g., the tabs 41A, 41B) for mounting the respective interface on the mounting construction (e.g., the recesses 21A, 21B) of a single spectrometer 12.

As explained below, the corn interface 14 is configured to receive the ear of corn C so that the corn is located in the interior space of the mount interface 40 between the arm portions 40B. The arm portions 40B are resiliently bendable with respect to the base portion 40A and away from one another to accommodate ears of corn C of different sizes. In one or more embodiments, the corn interface 14 (e.g., the arm portions 40B) is configured to grip and hold the ear of corn C in place relative to the spectrometer 12 as the spectrometer analyzes the ear of corn. The base portion 50 defines a transmission opening 46 and a detection opening 48. When the interface 14 is mounted on the spectrometer 12, the transmission opening 46 is operatively aligned with the radiation source 26 for conveying radiation from the source through the transmission opening. In addition, the detection opening 28 is operatively aligned with the detector 48 so that the detector is configured to detect a radiation spectrum through the detection opening. It will be understood that in other embodiments, the mount interface could define additional openings and/or a single opening configured for alignment with both the radiation source 26 and detector 28 of the spectrometer 12.

Figure 8:
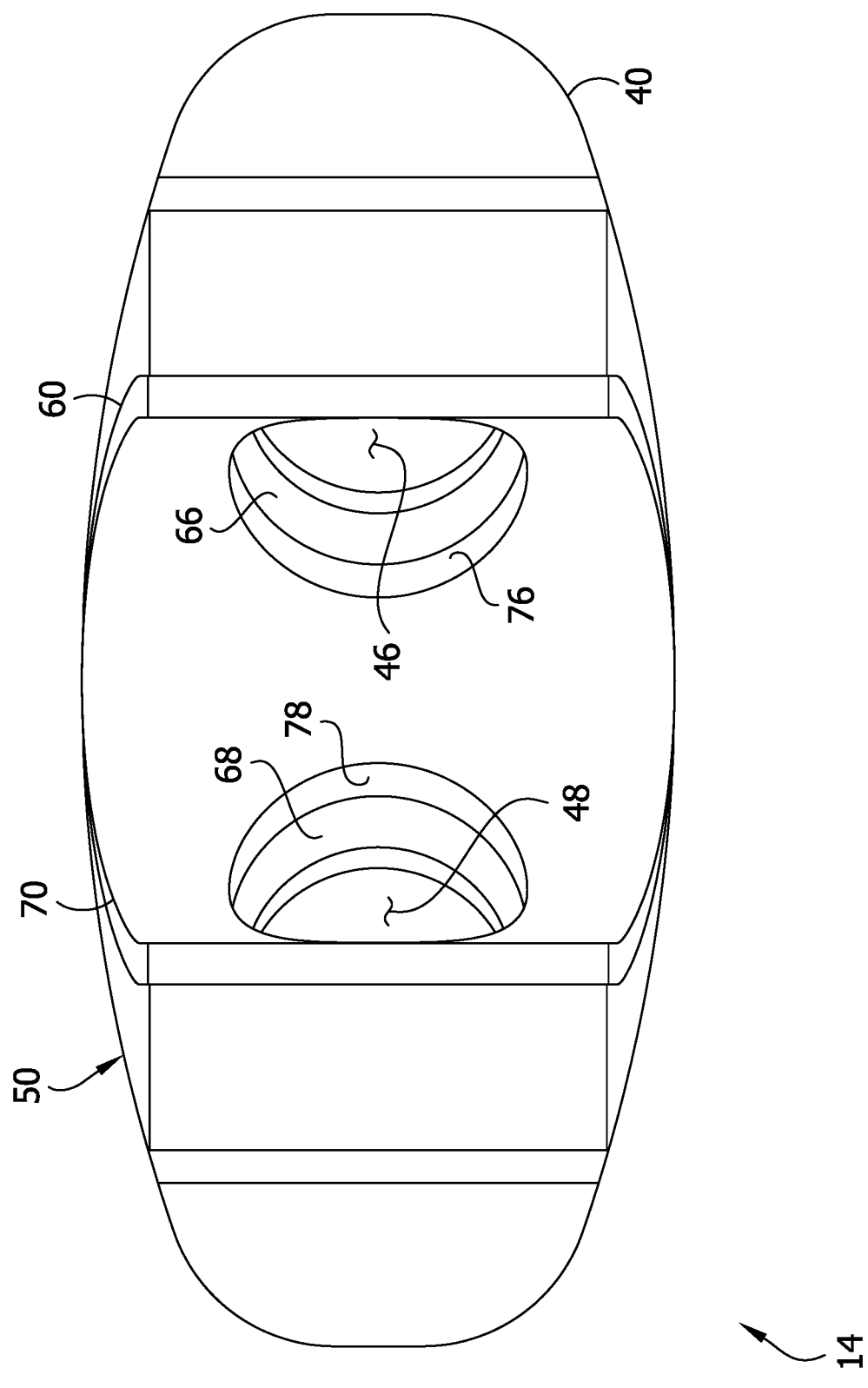
FIG. 8 is a front elevational view of the corn interface.
Figure 9:
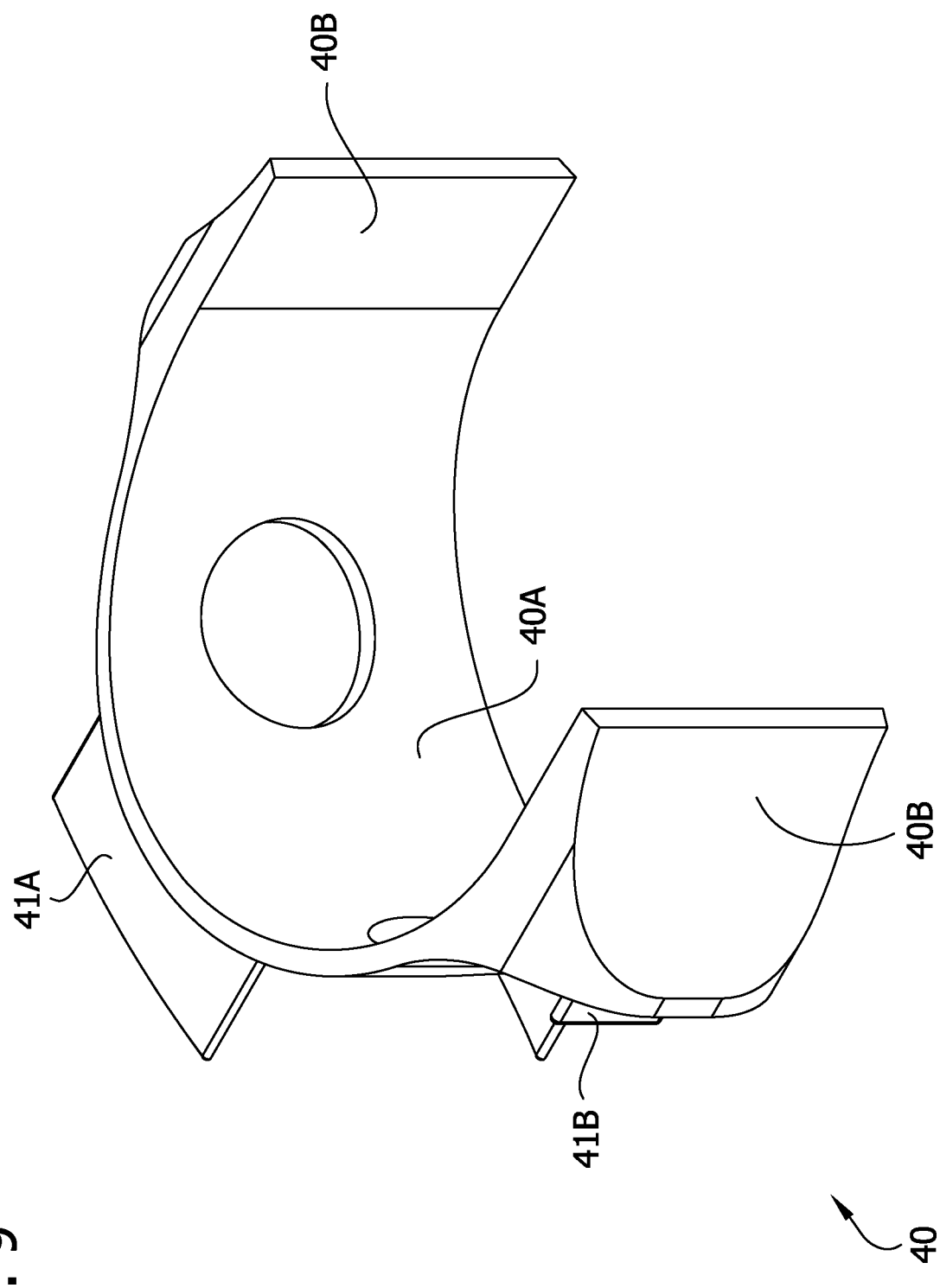
FIG. 9 is a perspective of a mount of the corn interface.

Referring to FIGS. 6-8, the corn interface 14 also includes a gasket, generally indicated at 50, attached to the mount interface 40 for operatively engaging the ear of corn C in use. The gasket 50 is generally U-shaped and comprises an arcuate proximal base portion 50A, and first and second arm portions 50B extending from the base portion. The gasket 50 has a thickness T (FIG. 7) extending between an exterior surface 50i, to which the mount interface 40 is attached, and an interior surface 50ii defining an interior space in which the ear of corn C is received. In use, the corn C is received in the interior space of the gasket 50, between the arm portions 50B and conformingly engages the interior surface 50ii defined by the base portion 50A and proximal segments of the arm portions.

Suitably, the illustrated gasket 50 is resiliently flexible to separate the arms from one another a suitable distance (and increase the interior space defined by the gasket) to accommodate ears of corn C of different sizes and shapes. Because the mount interface 40 is resiliently flexible, the opening between the arm portions 50B of the gasket can expand to receive an ear of corn C by bending the arm portions 40B of the mount interface 40 outwardly. When the arm portions 40B are released after bending, the gasket 50 resiliently returns toward its original shape. The gasket 50 is resiliently compressible to generally conform to the circumference of the corn C so that the interior surface 50ii of the gasket intimately contacts the corn. The light signals pass from the light source 26 through an opening in the foam 60/gasket 50 sandwich and are detected through an opening in the foam 60/gasket 50 sandwich in front of the detector 28. As explained below, the foam 60/gasket 50 defines at least one opening (including both the light source 26 area and the detector 28 area) extending through the entire thickness. The at least one opening is shaped and arranged for conveying radiation from the radiation source 26 to the corn C connected to the gasket 50 and/or detecting a radiation spectrum from the corn through the gasket using the detector 28.

In the illustrated embodiment, the gasket 50 is formed from two pieces that are joined together (e.g., adhered, fused, bonded, etc.). The gasket 50 comprises a backing member 60 that defines the exterior surface 50i of the gasket, and a liner or seal 70 that defines the interior surface 50ii of the gasket. The backing member 60 is resiliently compressible and sandwiched between the seal 70 and the mount interface 40. The seal member 70 conformingly engages the ear of corn C to form an optical seal between the corn and the spectrometer 12. It will be understood that in other embodiments one or more than two pieces can be used to form the backing portion and seal portion of the gasket.

Figure 10:
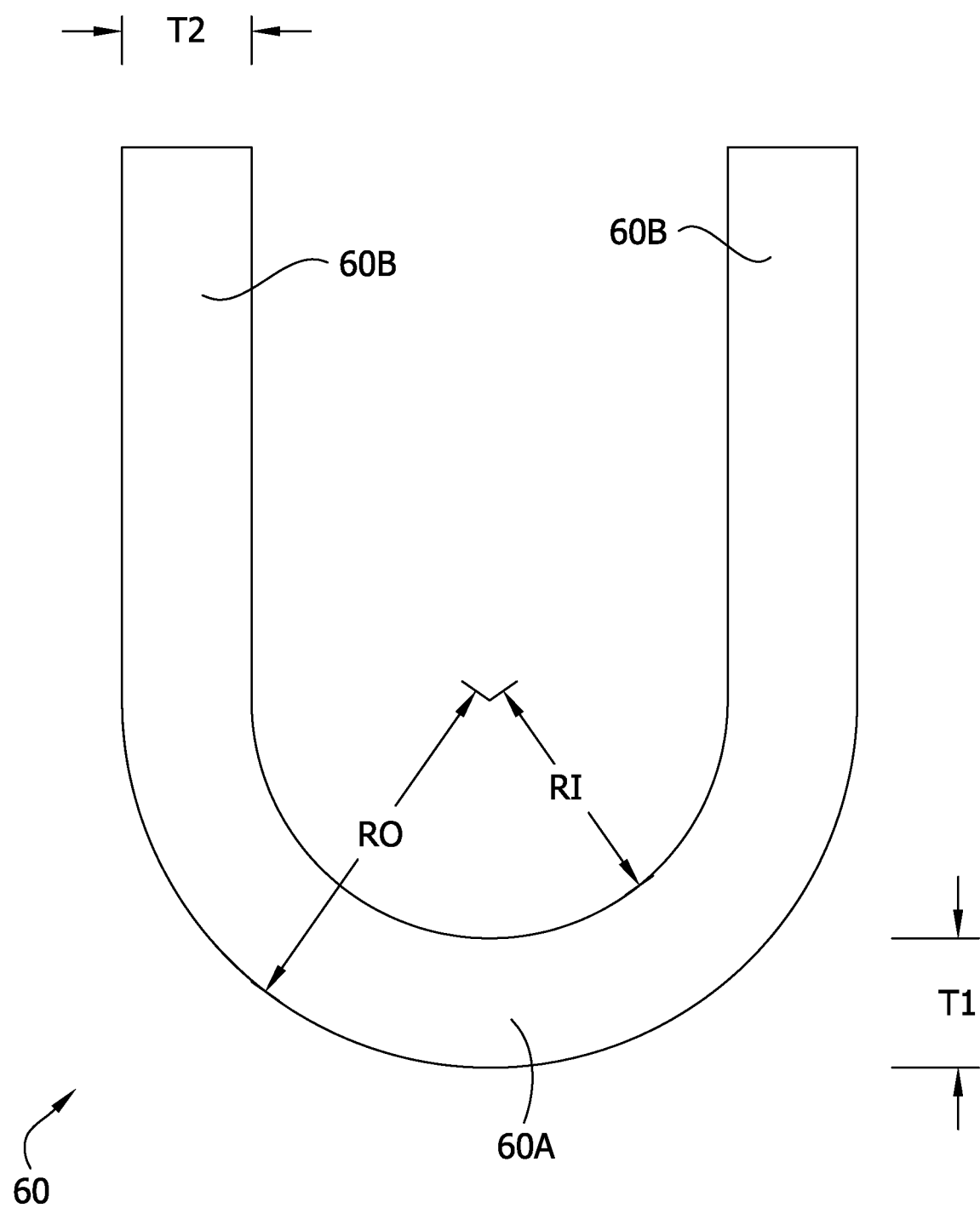
FIG. 10 is a top plan view of a backing member of a gasket of the interface.
Figure 11:
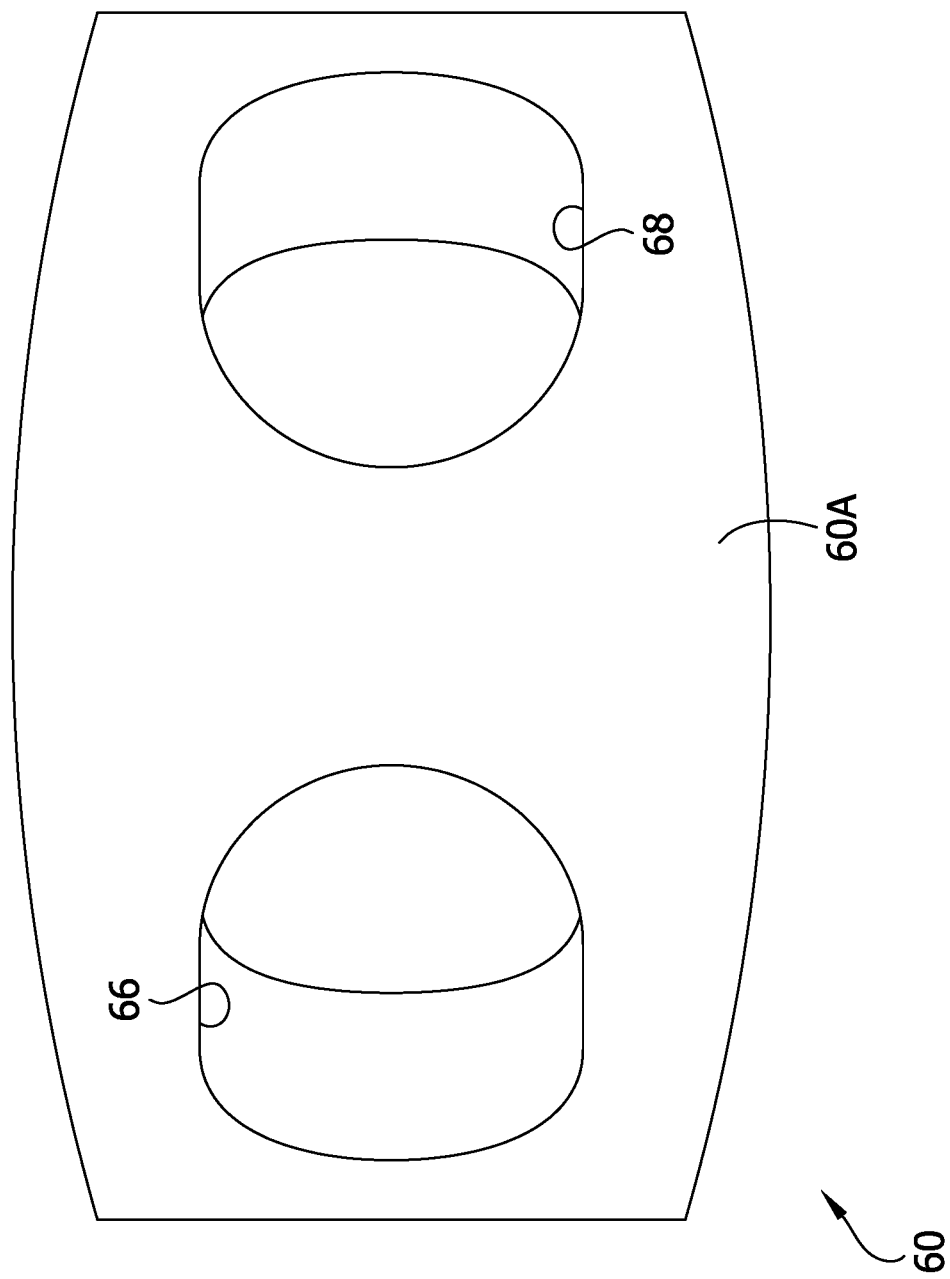
FIG. 11 is a front elevational view of the backing member.
Figure 14:
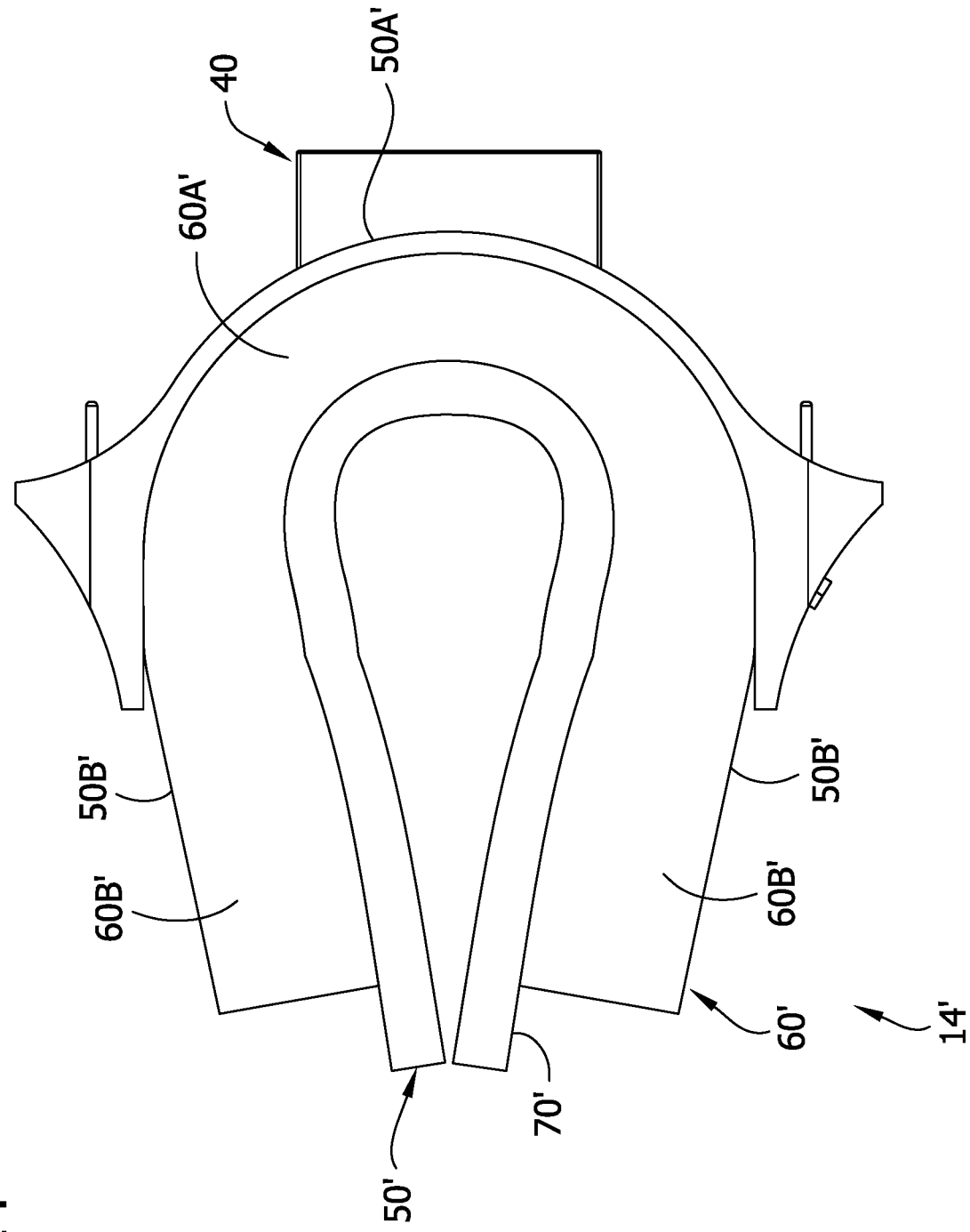
FIG. 14 is a top plan view of another embodiment of an interface used interchangeably with the interface of FIGS. 6-8.

Referring to FIGS. 10 and 11, the backing member 60 comprises a generally U-shaped body of compressible foam (e.g., super-cushioning polyurethane foam). In the illustrated embodiment, the backing member 60 is light impervious and formed to be resiliently biased to have the illustrated U-shape (e.g., the backing member 60 is molded or cut to shape using a water-jet process or other machining process), rather than bending a flat strip of foam material to the desired shape. Forming the backing member 60 to have an inherent U-shape instead of bending a foam strip to form a U-shape may enhance the quality of the optical seal formed between the gasket 50 and the corn C in use, as well as optimizing the openings for the radiation source (46, 66) and the detector (48, 68). The backing member 60 has an arcuate base portion 60A and first and second arm portions 60B. In the illustrated embodiment, the arm portions 60B extend generally parallel to one another. In other embodiments, the arm portions 60B can extend at an angle to one another (e.g., the arm portions 60B' of a backing member 60' of the interchangeable interface 14' converge inwardly as they extend away from the base portion 60A' as shown in FIG. 14). Referring to FIG. 10, the base portion 60A has a first thickness T1 and the arm portions have a second thickness T2 that is greater than the first thickness (e.g., in one embodiment, thickness T2 is at least about 0.1 inches greater than the thickness T1). Suitably, in the illustrated embodiment the thickness of the backing member 60 gradually tapers from the second thickness T2 to the first thickness between the arm portions 60B and the base portion 60A. For example, in one embodiment the thickness may taper from about 0.625 in (the first thickness T1) to about 0.50 in (the second thickness T2). In another embodiment, the thickness may taper from about 0.75 in (the first thickness T1) to about 0.50 in (the second thickness T2). In another embodiment, the thickness may be constant and measure about 0.5 in. The base portion 60A has an inner radius RI and an outer radius RO that is equal to the inner radius plus the first thickness T1. In one embodiment, the inner radius RI is in an inclusive range of from about 0.85 inches to about 1.15 inches (e.g., about 0.92 inches).

Referring to FIG. 11, the base portion 60A of the backing member 60 defines openings 66, 68 configured to be aligned with the openings 46, 48 of the mount interface 40 for operatively coupling the spectrometer 12 to the ear of corn C in use. The illustrated base portion 60A defines a transmission opening 66 and a spaced apart detection opening 68. When the interface 14 is mounted on the spectrometer 12, the transmission opening 66 is operatively aligned with the transmission opening 46 and the radiation source 26 for conveying radiation from the radiation source through the backing member 60. In addition, the detection opening 68 is operatively aligned with the detection opening 48 and the detector 28 so that the detector is configured to detect a radiation spectrum through the backing member 60. It will be understood that in other embodiments, the backing member of the gasket could define additional openings and/or a single opening configured for alignment with both the radiation source and detector of the spectrometer.

Referring to FIGS. 6-18 and 14 and as discussed above, in certain embodiments the moisture meter 10 includes a plurality of interchangeable interfaces 14, 14' for operatively connecting the spectrometer 12 to ears of corn C of different sizes. In one embodiment, each of the interchangeable interfaces 14, 14' includes a gasket 50, 50' having a backing member 60, 60' and a sealing member 70, 70'. To vary the geometry of the interchangeable interfaces 14 for receiving ears of corn C of different sizes, the backing members 60, 60' of the interchangeable interfaces 14, 14' can have different first and second thicknesses T1, T2, different inner and outer radii RI, RO, and/or different arm portion orientations (e.g., the arm portions 50B of the gasket 50 of one interface 14 can be oriented parallel as shown in FIG. 7 while the arm portions 50B' of the gasket 50' another interface 14' can converge toward one another as they extend away from the base portion 50A' as shown in FIG. 14). Additionally, the shape and arrangement of the seal member 70, 70' can vary between the interchangeable corn interfaces 15 to accommodate ears of corn of different shapes and sizes. In one or more embodiments, as long as the commonly sized mounting components (e.g., tabs 41A, 41B) are the same size for each of the corn interfaces 15, the size and shape of the mounting interfaces can also vary among the interchangeable corn interfaces to accommodate ears of corn of different shapes and sizes.

Figure 12:
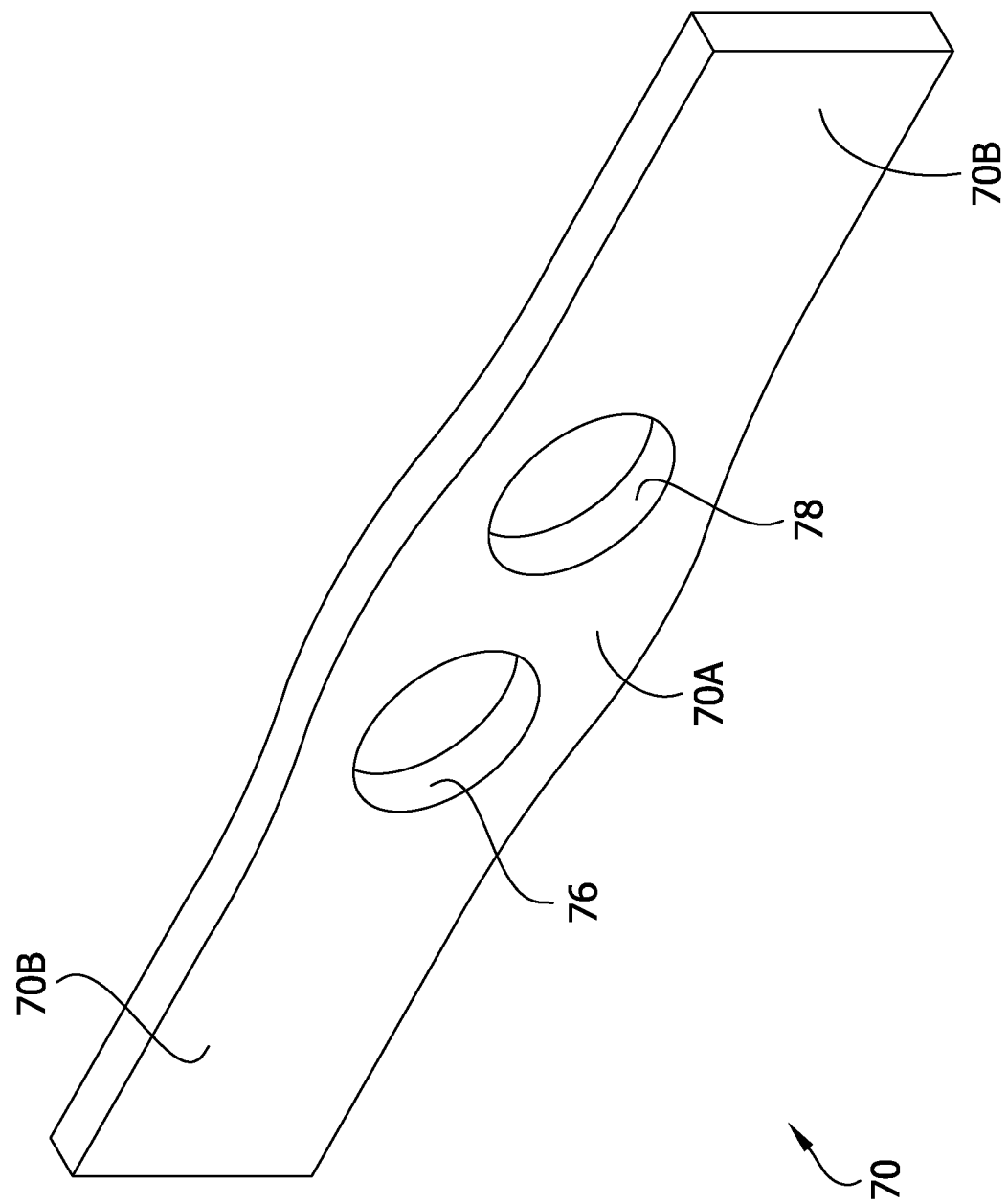
FIG. 12 is a perspective of a seal of the gasket.

Referring to FIG. 12, the seal 70 comprises a flat strip of opaque material (e.g., Viton® synthetic rubber) configured for forming an optical seal when pressed against the ear of corn. For example, in one or more embodiments, the material is flexible and may be resiliently compressible (such as less compressible than the backing member 60) so that it is capable of repeatedly being pressed against ears of corn C to form optical seals with each ear of corn without undergoing plastic or fatigue-induced permanent deformation that would inhibit the material's ability from forming an optical seal with additional ears of corn. Suitably, the seal 70 comprises a robust material that can withstand being pressed against the sometimes rough surface of exposed kernels of corn C on an ear without tearing. The seal 70 includes a central portion 70A and first and second end portions 70B extending outward from the central portion. In the illustrated embodiment, the seal 70 is attached (e.g., adhered or otherwise bonded) to the backing member 60 during manufacture so that the central portion 70A is attached to the base portion 60A and the end portions 70B are attached to the arm portions 60B. After being attached to the backing member 60, the seal 70 generally conforms to the shape of the backing member (e.g., has a U-shaped configuration; FIGS. 6-8). In the illustrated embodiment, the seal 70 has a substantially constant thickness (e.g., a thickness in an inclusive range of from about 0.1 inches to about 0.3 inches), while the foam 60 can vary in thickness for a given interface. In other embodiments, the thickness of the seal 70 may vary along the seal. The central portion 70A of the seal 70 defines a transmission opening 76 and a detection opening 78. When the assembled interface 14 is mounted on the spectrometer 12, the transmission opening 76 is operatively aligned with the radiation source 26 and the transmission openings 46, 66 of the mount interface 40 and the backing member 60 for conveying radiation from the radiation source through the aligned transmission openings. In addition, the detection opening 78 is operatively aligned with the detector 28 and the detection openings 48, 68 so that the detector is configured to detect a radiation spectrum through the aligned detection openings.

Figure 13:
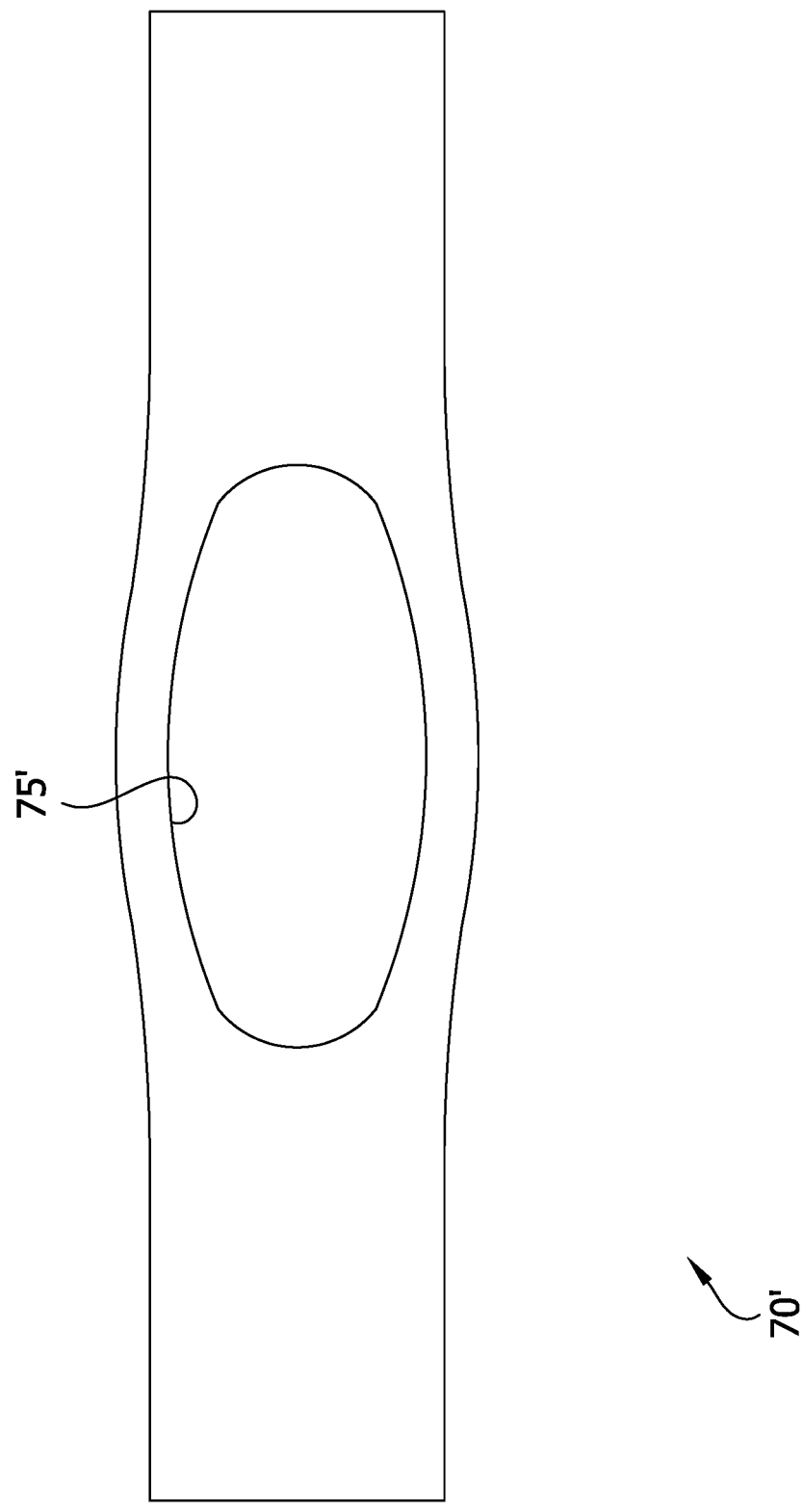
FIG. 13 is a front elevational view of another embodiment of a seal similar to the seal shown in FIG. 12.

As shown in FIG. 13, in other embodiments a seal 70' comprises a single opening 75' configured for alignment with both the radiation source 26 and the detector 28 of the spectrometer 12. In certain embodiments, the seal 70' is used with a backing member and a mount interface (not shown) that each likewise define a single opening that corresponds generally to the size and shape of the single opening 75'. In other embodiments, the seal can define other numbers of openings (e.g., more than two openings) for operatively coupling the corn C to the spectrometer 12.

Referring to FIGS. 3 and 12, when the corn interface 14 operatively couples the ear of corn C to the spectrometer 12, the central portion 70A of the seal 70 extends circumferentially around a portion of the ear of corn C and engages the kernels. When the corn interface 14 is pressed against the corn C, the seal 70 forms an optical seal at the interface with the corn C that extends around the transmission opening 76 and the detection opening 78. The optical seal inhibits ambient light from passing between the corn C and the corn interface 14 and being detected by the spectrometer 12. Thus, the corn interface 14 functions as a coupling for operatively coupling the spectrometer 12 to the ear of corn C to control the conditions at the location of the corn where the detector 28 detects a radiation spectrum to enhance moisture measurement accuracy. Though every ear of corn C has a different exterior shape, the configurations of the mount 40, the backing member 60, and the seal 70 enable the corn interface 14 to form effective optical seals with different ears of corn of one or more varieties. Some varieties of corn have substantially different outer diameters than others. Including a plurality of interchangeable interfaces 14, 14' with the moisture meter 10 enables the device to form consistently effective optical seals with even different varieties of corn C whose characteristic dimensions vary considerably.

In one embodiment, the moisture meter 10 is used to measure an amount of moisture in corn C while the corn is growing in a field, without separating any kernels from the growing plant. Initially, the user or other moisture tester exposes kernels on an ear of corn C growing in the field. If not already installed, the user installs an interchangeable interface 14 on the spectrometer 12 that is suitable for the variety of corn C growing in the field. The user then operatively couples the spectrometer 12 to the exposed kernels using the interface 14. Specifically, the ear of corn C is inserted between the arm portions 50B of the gasket 50 until the exposed kernels engage the central portion 70A of the seal 70. In some embodiments, this requires bending the arm portions 50B radially outward to accommodate the corn C. The user engages the gasket 50 against the corn C to form an optical seal between the spectrometer 12 and the corn. As the gasket 50 is pressed against the corn C, the seal 70 and/or the backing member 60 may compress to conform to the ear. In addition or in the alternative, the arm portions 40B of the mount interface 40 may bend or flex outwardly so that the seal 70 conforms more closely to the ear of corn C. The optical seal at the juncture of the seal 70 and the corn C blocks at least some of (in some embodiments, substantially all of) the ambient light from passing through the optical seal between the ear of corn C and the spectrometer 12. For example, the optical seal inhibits ambient light from passing through the detection openings 48, 68, 78 into the detector 28.

With the spectrometer 12 operatively coupled to the ear of corn C, the user can measure an amount of moisture in the corn using the spectrometer. When the user depresses the trigger 22, the measurement processor 30 actuates the radiation source 26 and the detector 28. The radiation source 26 transmits NIR radiation through the transmission openings 46, 66, 76 to the corn C. A portion of the NIR radiation that is reflected by the water in the corn C. The detector 28 detects an NIR spectrum through the detection openings 48, 68, 78 and transmits a signal representative of the detected radiation spectrum to the measurement processor 30. The measurement processor 30 analyzes the received signal to determine an amount of NIR radiation that is absorbed and/or reflected by the corn C and uses the determined amount of absorbed radiation to determine an amount of moisture in the corn. In the illustrated embodiment, the measurement processor 30 determines a moisture percentage by weight of the corn, stores the determined amount of moisture in the memory 32, and displays the determined amount of moisture on the display 24.

In some embodiments, the user repeats the process of nondestructively measuring the amount of moisture in corn C from ears sampled at multiple locations throughout the field to determine an average moisture content for the field. In each case, the user measures the amount of moisture for the ear of corn C while the ear of corn is growing on a corn plant, without removing the ear of corn from the corn plant and/or separating the kernels of corn from the ear. The user can use the moisture data to evaluate when the corn C is ready for harvest (e.g., when the corn will sell at the best possible price). For example, the user can compare the determined moisture percentage by weight to a threshold moisture percentage by weight associated with an optimal price at sale (e.g., a threshold of 25% moisture by weight). When the measured moisture percentage is greater than the threshold moisture percentage, the user may choose to not harvest the corn. The user may choose to harvest the corn only after the determined moisture percentage is less than or equal to the threshold moisture percentage, thus maximizing the price of the harvested corn at sale.

Although the moisture meter 10 is described above as being used for measuring moisture in ears of corn C growing in a field, it will be understood that the moisture meter could also be used in other contexts. For example, in one embodiment, the moisture meter 10 is used to measure the moisture in corn C growing on ears in a greenhouse. The gasket 50 is suitably configured to form an optical seal that limits the effect of light from greenhouse luminaires (e.g., high pressure sodium lights, metal halide lights, red and blue LED lights, etc.) on the moisture measurement. In addition, in certain embodiments, the moisture meter 10 is used to measure the moisture in a detached ear of corn. In one embodiment, the corn interface 14 is replaced with a corn interface comprising a gasket of generally the same configuration as the gasket 50, but having a substantially smaller inner radius RI such that the gasket is sized and arranged for forming an optical seal about the stalk of the corn instead of the ear of corn. Using this corn interface, the moisture meter 10 can be used to measure the moisture in the corn stalk instead of the corn ear. In still other embodiments, the interface 14 is replaced with an interface configured for forming an optical seal with another crop (e.g., a fruit such as a tomato, melon, etc., or a vegetable such as a pepper, a cucumber etc.) and the measurement processor 30 is programed for measuring the amount of moisture in the crop based on the signal representative of the detected optical spectrum. In another embodiment, the moisture meter 10 is used to monitor the drying of corn ear post-harvest to ensure that seed quality (e.g. germination rate) is maintained. Seed quality could be compromised if the seeds are dried too long (i.e. to too low a moisture level).

Referring to FIG. 1, to validate the accuracy of the moisture meter 10, the moisture meter 10 was used to measure moisture for plurality of ears of dent corn C and the moisture measurements determined by the moisture meter were compared with moisture measurements determined by conventional methods that are considered to be reliable and accurate by those skilled in the art. These measurements have been demonstrated for the % corn moisture rage of 10-65%, by using specific % moisture model ranges of 10-25%, 20-45%, and 40-65%. Some examples are presented in tables 1 and 2 below. Specifically, Table 1 below shows a comparison of moisture measurements of 39 sample ears of corn C in units of moisture percentage by weight using the moisture meter 10 and a conventional method of oven drying the corn and determining the weight loss on drying. Table 2 below shows a comparison of moisture measurements of 21 sample ears of corn C in units of moisture percentage by weight using the moisture meter 10 and a Perten DA 7200 benchtop optical moisture measurement instrument sold by Perten Instruments Group of Stockholm, Sweden. Comparing the predicted % moisture values based on NIR data with actual % moisture (based on oven drying) in Table 1, the compared % moisture measurements have a statistically equivalent P value of greater than 0.05 (0.098). Data resulting from initial testing of sweet corn at two different sites per ear, using a moisture model being developed for sweet corn is presented in Table 3. In each comparison, the compared moisture measurements have a statistically equivalent P value of greater than 0.05 (for the values in Table 1, the P value is 0.192; for the values in Table 2 the P value is 0.167). Accordingly, the nondestructive moisture measurements obtained using the meter 10 have been determined to be about as accurate as conventional benchtop methods of measuring the amount of moisture in corn, but without the destroying the sample corn before harvest in order to obtain the measurements.

TABLE 1

Comparison of Corn Moisture Measurements Using Meter 10 and Conventional Weight on Oven Drying

| Sample | Moisture Percentage by Weight Using Meter 10 | Moisture Percentage by Weight Using Oven Drying |
|---|---|---|
| 1 | 29.5 | 27.3 |
| 2 | 27.2 | 25.9 |
| 3 | 17.2 | 14.9 |
| 4 | 16.0 | 17.2 |
| 5 | 15.8 | 15.4 |
| 6 | 21.0 | 30.7 |
| 7 | 16.6 | 25.1 |
| 8 | 18.1 | 22.8 |
| 9 | 19.0 | 29.2 |
| 10 | 16.2 | 25.7 |
| 11 | 15.0 | 15.5 |
| 12 | 15.8 | 16.1 |
| 13 | 15.0 | 15.6 |
| 14 | 14.7 | 12.5 |
| 15 | 15.7 | 16.4 |
| 16 | 16.5 | 18.6 |
| 17 | 15.8 | 15.6 |
| 18 | 15.7 | 17.7 |
| 19 | 16.3 | 15.8 |
| 20 | 15.5 | 16.9 |
| 21 | 11.3 | 9.3 |
| 22 | 25.8 | 20.3 |
| 23 | 14.8 | 12.3 |
| 24 | 15.0 | 13.7 |
| 25 | 14.0 | 12.0 |
| 26 | 14.0 | 16.4 |
| 27 | 12.4 | 9.5 |
| 28 | 14.6 | 15.3 |
| 29 | 14.1 | 13.6 |
| 30 | 14.6 | 14.6 |
| 31 | 57.4 | 58.8 |
| 32 | 60.8 | 59.5 |
| 33 | 53.8 | 54.2 |
| 34 | 46.9 | 48.2 |
| 35 | 41.8 | 42.2 |
| 36 | 38.9 | 40.6 |

TABLE 1-continued

Comparison of Corn Moisture Measurements Using Meter 10 and Conventional Weight on Oven Drying

| Sample | Moisture Percentage by Weight Using Meter 10 | Moisture Percentage by Weight Using Oven Drying |
|---|---|---|
| 37 | 44.2 | 45.5 |
| 38 | 41.7 | 43.0 |
| 39 | 39.2 | 40.6 |

TABLE 2

Comparison of Corn Moisture Measurements Using Meter 10 and Perten DA 7200 Benchtop Instrument

| Sample | Moisture Percentage by Weight Using Meter 10 | Moisture Percentage by Weight Using Perten DA 7200 |
|---|---|---|
| 31 | 21.2 | 22.7 |
| 32 | 12.3 | 14.4 |
| 33 | 23.6 | 22.8 |
| 34 | 24.2 | 23.4 |
| 35 | 20.5 | 20.1 |
| 36 | 26.8 | 24.3 |
| 37 | 16.4 | 18.9 |
| 38 | 22.1 | 24.1 |
| 39 | 25.0 | 22.8 |
| 40 | 24.8 | 27.5 |
| 41 | 21.0 | 23.6 |
| 42 | 29.5 | 28.3 |
| 43 | 27.2 | 25.5 |
| 44 | 17.2 | 14.9 |
| 45 | 16.0 | 17.8 |
| 46 | 15.8 | 15.2 |
| 47 | 21.0 | 28.5 |
| 48 | 16.6 | 22.6 |
| 49 | 18.1 | 25.6 |
| 50 | 19.0 | 28.4 |
| 51 | 16.2 | 22.6 |

TABLE 3

Comparison of Sweet Corn Moisture Measurements Using Meter 10 and Conventional Weight on Oven Drying

| Sample | Moisture Percentage by Weight Using Meter 10 | Moisture Percentage by Weight Using Oven Drying |
|---|---|---|
| 1 | 57.8 | 57.2 |
| 1 | 57.8 | 57.0 |
| 2 | 55.7 | 55.9 |
| 2 | 58.0 | 56.5 |
| 3 | 52.4 | 53.6 |
| 3 | 60.2 | 61.2 |

Figure 15:
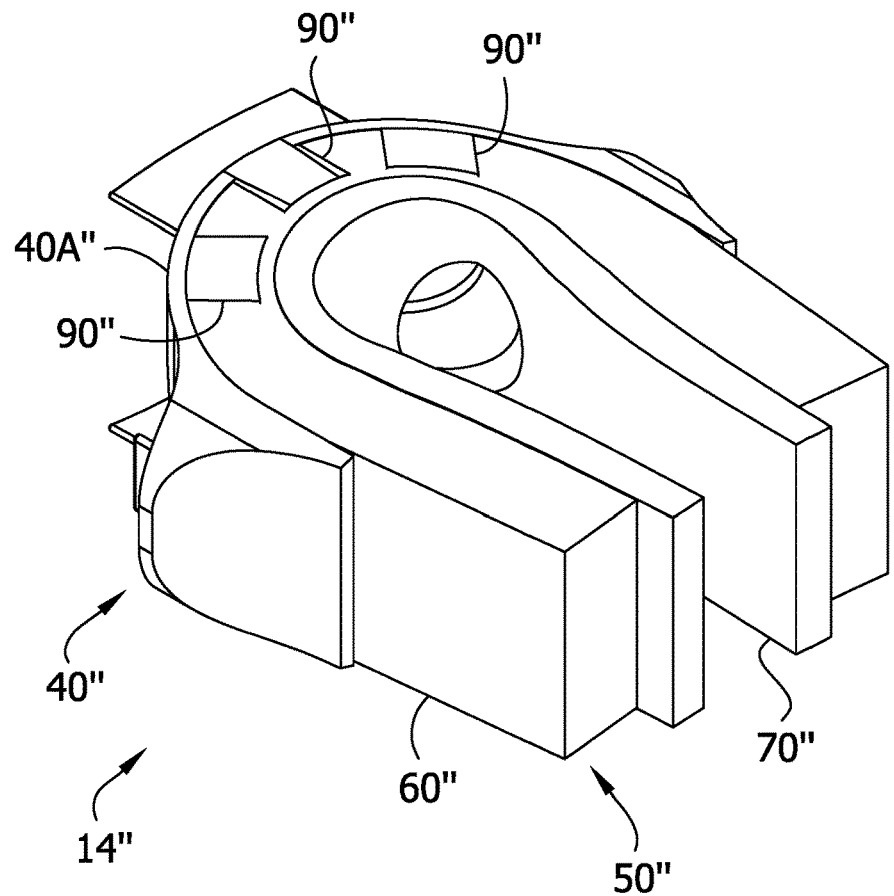
FIG. 15 is a perspective of another embodiment of a corn interface used interchangeably with the interfaces of FIGS. 6-8 and FIG. 14.
Figure 16:
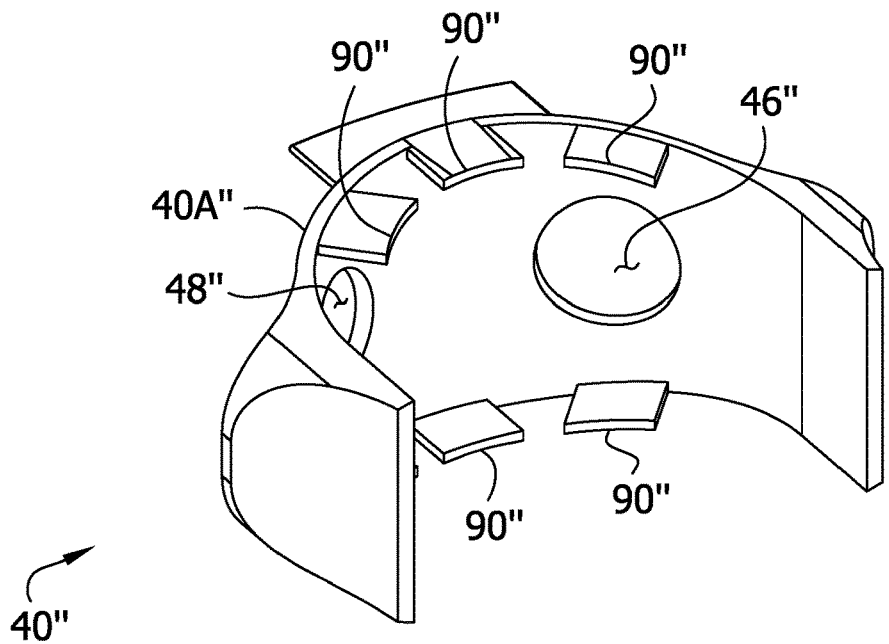
FIG. 16 is a perspective of a mount interface of the corn interface of FIG. 15.

Referring to FIGS. 15 and 16, another embodiment of a corn interface that can be used with the moisture meter 10 is generally indicated at reference number 14". The corn interface 14" is substantially identical to the corn interface 14, except for the differences that are discussed below. In one or more embodiments, the mount interface 40" of the corn interface 14" includes one or more stops 90" that facilitate positioning an ear of corn C at a proper position in the corn interface for measuring the moisture content of the corn. In the illustrated embodiment, the mount interface 40" includes three stop tabs 90" at spaced apart locations along the top of the base portion 40A" of the mount interface and three stop tabs at spaced apart locations along the bottom of the base portion of the mount interface. Along the top and the bottom of base portion 40A", the illustrated mount interface 40" includes a first stop tab 90" that is generally aligned with the transmission opening 46", a second stop tab that is generally aligned with the detection opening 48", and a third stop tab that is spaced apart between the first and second stop tabs. Each of the stop tabs 90" projects inwardly toward the interior of the corn interface 14" from the base portion 40A" of the mount interface 40". In the illustrated embodiment, the top stop tabs 90" extend inwardly along the top of the gasket 50" and the bottom stop tabs extend inwardly along the bottom of the gasket. Each of the stop tabs 90" extends inwardly to a free end that is spaced apart outwardly from the interior surface of the gasket 50" (e.g., in the illustrated embodiment, the free ends of the stop tabs are located adjacent the interior surface of the backing member 60" and are slightly spaced outwardly from the exterior surface of the seal 70"). In one or more embodiments, the stops 90" are substantially rigid. When an ear of corn C is positioned in the corn interface 14", the free ends of the stop tabs 90" limit the extent to which the ear can be pushed rearward toward the base portion 40A" of the mount interface 40". The stop tabs 90" likewise limit the extent to which the corn ear C can compress the gasket 50". Suitably, the stop tabs 90" stop rearward movement of the corn ear C at a position in which the corn ear is properly positioned for the moisture meter 10 to measure the composition of the corn ear. The corn interface 14" can be used interchangeably with the corn interfaces 14, 14' in certain embodiments.

Figure 17A:
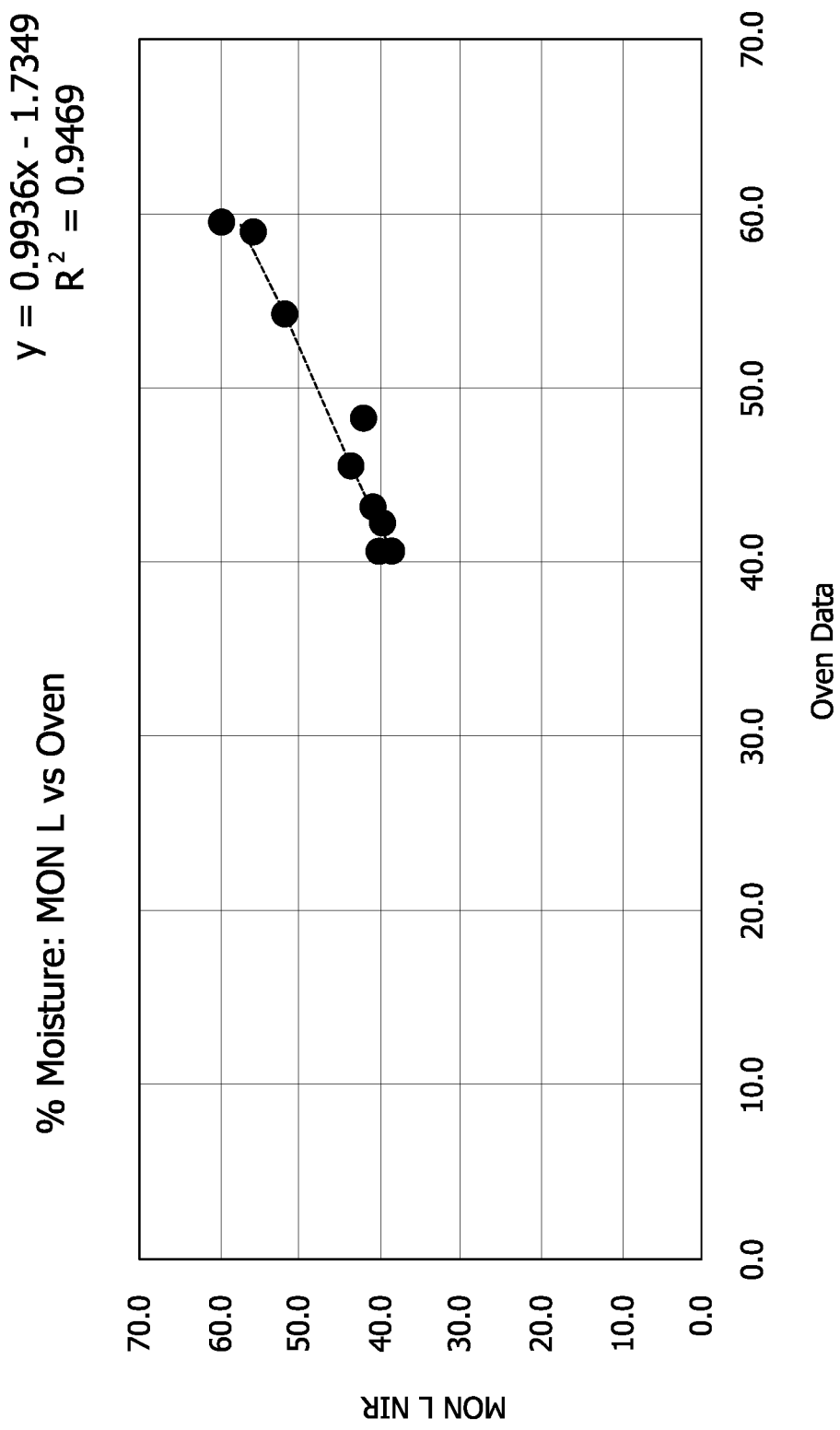
FIG. 17A is a graph comparing moisture measurements taken using a moisture meter equipped with a corn interface of FIGS. 6-8 with moisture measurements taken using an oven drying method.
Figure 17B:
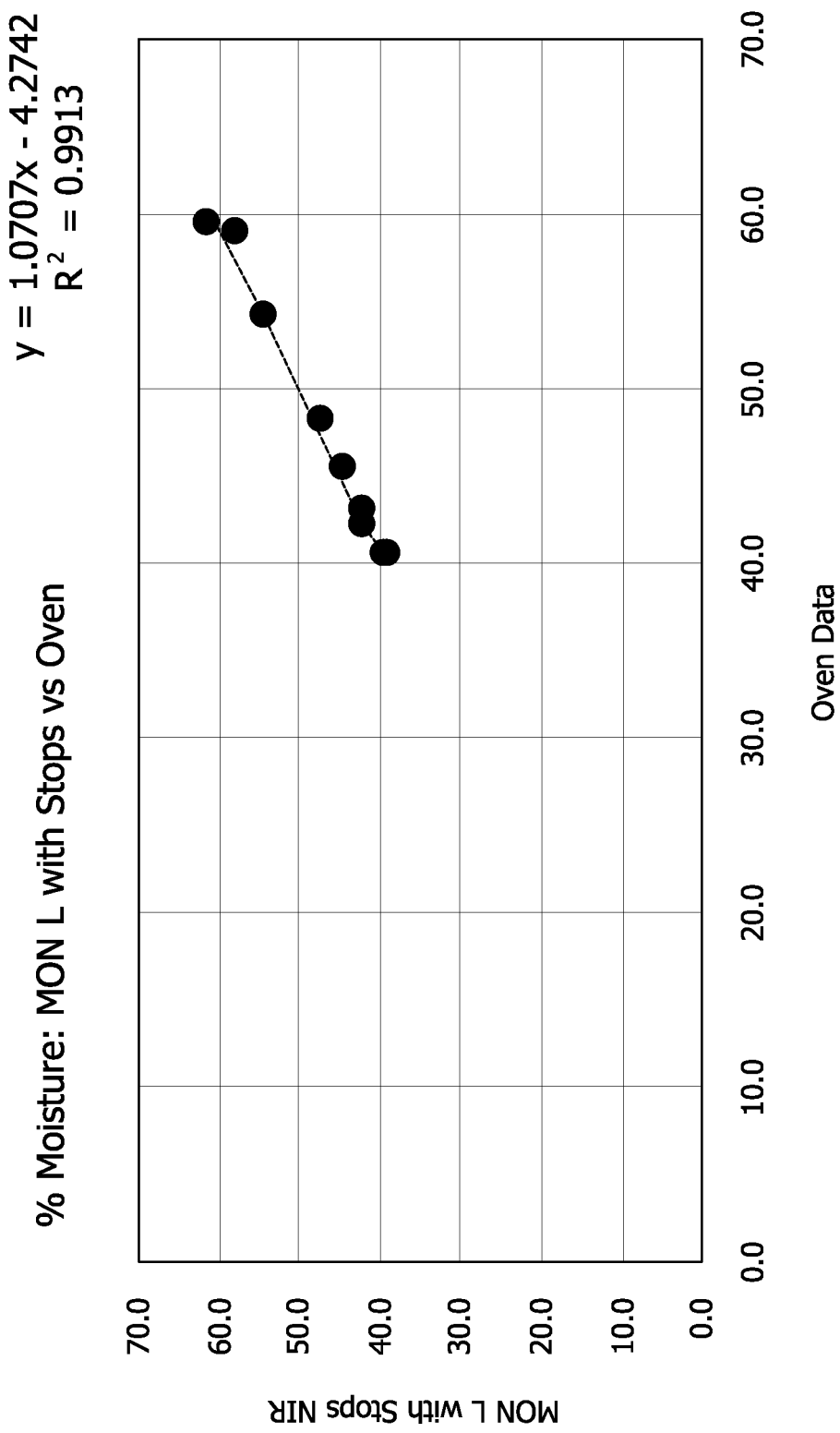
FIG. 17B is a graph comparing moisture measurements taken using a moisture meter equipped with a corn interface of FIGS. 15 and 16 with moisture measurements taken using an oven drying method.

Referring to FIGS. 17A and 17B, to test the effect of the stop tabs 90" on the quality of moisture measurements that are taken by the moisture meter 10, the moisture content of several ears of corn were measured using the moisture meter equipped with the corn interface 14 and the corn interface 14", and these measurements were compared to control measurements taken using the oven drying method described above. FIG. 17A shows a comparison of the moisture measurements made using the corn interface 14 and the oven drying control measurements; and FIG. 17B shows a comparison of the moisture measurements made using the corn interface 14" and the oven drying control measurements. As can be seen, the measurements taken with the moisture meter 10 using both the corn interface 14 and the corn interface 14" tracked very closely to the control measurements. The measurements taken with the moisture meter 10 equipped with the corn interface 14" were found to be slightly more accurate than the measurements taken with the moisture meter 10 equipped with the corn interface 14. It is believed that the stop tabs 90" contributed to the improved measurement accuracy by engaging the corn to position the corn at a proper position for obtaining accurate moisture measurements.

It will be appreciated that the stop tabs 90" of the mount interface 40 are but one mechanism that can facilitate properly positioning a corn ear with respect to the moisture meter 10. Other stop configurations can also be used in one or more embodiments. In addition, in certain embodiments, it is contemplated that the corn interface can comprise a hinged clamshell structure that is configured to close around the girth of an ear of corn and properly position the corn ear in the clamshell for moisture measurement.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method of measuring moisture in corn, the method comprising:
    operatively coupling an ear of corn to a spectrometer, by:
        engaging the ear of corn with a compressible gasket of a corn interface secured to the spectrometer; and
        forming, by the compressible gasket of the corn interface, an optical seal between the spectrometer and the ear of corn to substantially inhibit ambient light from being detected by the spectrometer; and
    determining an amount of moisture in the ear of corn with the spectrometer.

2. The method as set forth in claim 1, wherein the step of determining the amount of moisture comprises directing radiation from the spectrometer to the ear of corn through an opening in the interface.

3. The method as set forth in claim 2, wherein the step of determining the amount of moisture further comprises detecting a radiation spectrum through one of said opening in the interface and another opening in the interface.

4. The method as set forth in claim 1, further comprising exposing kernels of the ear of corn, wherein the step of operatively coupling the ear of corn to the spectrometer comprises operatively coupling the exposed kernels to the spectrometer.

5. The method as set forth in claim 1, wherein the step of determining an amount of moisture in the ear of corn comprises:
    generating, by the spectrometer, near infrared (NIR) radiation; and
    detecting the amount of generated NIR radiation that is absorbed or reflected by the ear of corn.

6. The method as set forth in claim 1, wherein the spectrometer is a near infrared (NIR) spectrometer; and
    wherein the step of determining an amount of moisture in the ear of corn comprises measuring an amount of NIR radiation that is absorbed or reflected by the ear of corn.

7. The method as set forth in claim 1, further comprising:
    operatively coupling the spectrometer to at least one other ear of corn while the at least one other ear of corn is being grown on a corn plant; and
    measuring an amount of moisture in said at least one other ear of corn with the spectrometer while the at least one other ear of corn is being grown on the corn plant.

8. A method of harvesting corn, the method comprising:
    (a) measuring moisture in the corn according to the method of claim 1;
    (b) determining whether the measured moisture in the corn is less than, equal to, or greater than a threshold amount of moisture for use in determining whether to harvest the corn.

9. A corn interface for operatively coupling a spectrometer to an ear of corn for measuring an amount of moisture in the corn, the interface comprising:
    a spectrometer interface configured to attach to the spectrometer; and
    a compressible gasket supported on the spectrometer interface, wherein the compressible gasket is configured to conformingly engage the ear of corn when pressed against the ear of corn to form an optical seal between the ear of corn and at least one of a radiation source and a radiation detector of the spectrometer.

10. The corn interface as set forth in claim 9, wherein the compressible gasket is generally U-shaped and comprises an arcuate base portion having first and second ends and first and second arm portions extending from the first and second ends, respectively.

11. The corn interface as set forth in claim 10, wherein the opening extends through the base portion.

12. The corn interface as set forth in claim 10, wherein the base portion of the compressible gasket is attached to the spectrometer interface.

13. The corn interface as set forth in claim 9, wherein the compressible gasket defines another opening spaced apart from said opening that extends through the thickness of the compressible gasket from the exterior surface through the interior surface, the other opening being shaped and arranged to be aligned with the spectrometer for conveying radiation from the radiation source of the spectrometer through the gasket when the spectrometer interface is attached to the spectrometer.

14. The corn interface as set forth in claim 9, wherein the compressible gasket comprises:
   a seal portion defining the interior surface of the compressible gasket and comprising a first material; and
   a backing portion proximal of the seal portion comprising a second material.

15. The corn interface as set forth in claim 14, wherein the first material comprises rubber and the second material comprises foam.

16. A moisture meter comprising the interface of claim 9 attached to the spectrometer.

17. A moisture meter for measuring moisture in corn, the moisture meter comprising:
   a hand-held housing;
   a corn interface mounted on the hand-held housing and having a thickness, the corn interface being configured to operatively couple to an ear of corn to form an optical seal between the ear of corn and the corn interface to inhibit ambient light from passing between the corn interface and the ear of corn;
   a radiation source supported on the hand-held housing and configured to convey radiation through to the corn when the corn is operatively coupled to the moisture meter;
   a detector mounted on the hand-held housing and configured to detect a radiation spectrum passing and to generate a signal representative of the detected radiation spectrum; and
   a measurement processor configured to receive the signal from the detector and to determine an amount of moisture in the corn based on the signal.

18. A method of measuring moisture in corn, the method comprising:
   operatively coupling an ear of corn to a spectrometer, by:
      engaging the ear of corn with a corn interface secured to the spectrometer; and
      forming an optical seal between the spectrometer and the ear of corn to substantially inhibit ambient light from being detected by the spectrometer; and
   determining an amount of moisture in the ear of corn with the spectrometer by directing radiation from the spectrometer to the ear of corn through an opening in the interface.

* * * * *